(12) United States Patent
Loupis et al.

(10) Patent No.: US 10,130,706 B2
(45) Date of Patent: Nov. 20, 2018

(54) BIOPHOTONIC MATERIALS AND USES THEREOF

(71) Applicant: KLOX TECHNOLOGIES INC., Laval (CA)

(72) Inventors: Nikolaos Loupis, Athens (GR); Remigio Piergallini, Grottammare Ascoli Piceno (IT); Éric DesRosiers, Quebec (CA)

(73) Assignee: KLOX TECHNOLOGIES INC., Laval, Québec (CA)

( * ) Notice: Subject to any disclaimer, the term of this patent is extended or adjusted under 35 U.S.C. 154(b) by 0 days.

(21) Appl. No.: 14/775,156

(22) PCT Filed: Mar. 14, 2014

(86) PCT No.: PCT/CA2014/000261
§ 371 (c)(1),
(2) Date: Sep. 11, 2015

(87) PCT Pub. No.: WO2014/138930
PCT Pub. Date: Sep. 18, 2014

(65) Prior Publication Data
US 2016/0030564 A1    Feb. 4, 2016

Related U.S. Application Data

(63) Continuation-in-part of application No. 14/204,741, filed on Mar. 11, 2014, now abandoned.
(Continued)

(51) Int. Cl.
*A61K 41/00* (2006.01)
*A61K 8/02* (2006.01)
(Continued)

(52) U.S. Cl.
CPC ........ *A61K 41/0057* (2013.01); *A61K 8/0212* (2013.01); *A61K 8/0216* (2013.01);
(Continued)

(58) Field of Classification Search
CPC . C09K 11/06; C09K 11/02; C09K 2211/1088; C09K 2211/145; A61K 41/0057
See application file for complete search history.

(56) References Cited

U.S. PATENT DOCUMENTS 2,877,221 A      3/1959  Lanbach
2,963,382 A *  12/1960  Switzer .................... C08K 5/17
                                                              427/157
(Continued)

FOREIGN PATENT DOCUMENTS

CA      2222027      6/1998
CA      2360202     12/1999
(Continued)

OTHER PUBLICATIONS

Mintel, "Gold Bear Gums," http://gnpd.com, Aug. 1, 2008 (3 pages).
(Continued)

*Primary Examiner* — C Melissa Koslow
(74) *Attorney, Agent, or Firm* — BCF LLP

(57) ABSTRACT

The present disclosure provides topical biophotonic materials and methods useful in phototherapy. In particular, the topical biophotonic materials of the present disclosure include a cohesive matrix, and at least chromophore which can absorb and emit light from within the topical biphotonic material, wherein the topical biophotonic material is elastic. The topical biophotonic materials and the methods of the present disclosure are useful for promoting wound healing and skin rejuvenation, as well as treating acne and various other skin disorders.

21 Claims, 8 Drawing Sheets

Related U.S. Application Data

(60) Provisional application No. 61/873,747, filed on Sep. 4, 2013, provisional application No. 61/786,197, filed on Mar. 14, 2013.

(51) Int. Cl.
| | | |
|---|---|---|
| *A61K 9/00* | (2006.01) | |
| *A61L 15/42* | (2006.01) | |
| *A61N 5/06* | (2006.01) | |
| *A61P 17/00* | (2006.01) | |
| *A61P 17/02* | (2006.01) | |
| *A61Q 19/08* | (2006.01) | |
| *A61K 8/49* | (2006.01) | |
| *A61Q 19/00* | (2006.01) | |
| *A61K 8/04* | (2006.01) | |
| *A61K 8/73* | (2006.01) | |
| *A61K 47/36* | (2006.01) | |
| *A61M 11/00* | (2006.01) | |
| *A61M 35/00* | (2006.01) | |

(52) U.S. Cl.
CPC .............. *A61K 8/042* (2013.01); *A61K 8/498* (2013.01); *A61K 8/735* (2013.01); *A61K 47/36* (2013.01); *A61M 11/00* (2013.01); *A61M 35/00* (2013.01); *A61N 5/062* (2013.01); *A61N 5/0616* (2013.01); *A61Q 19/00* (2013.01); *A61Q 19/08* (2013.01); *A61K 2800/434* (2013.01); *A61K 2800/81* (2013.01); *A61N 2005/0658* (2013.01); *A61N 2005/0662* (2013.01)

(56) References Cited

U.S. PATENT DOCUMENTS

| | | | |
|---|---|---|---|
| 3,293,127 A | | 12/1966 | Beck |
| 3,309,274 A | | 3/1967 | Brilliant |
| 3,372,125 A | | 3/1968 | Hill |
| 3,595,798 A | | 7/1971 | Smith et al. |
| 3,597,362 A | | 8/1971 | Rauhut et al. |
| 3,652,420 A | | 3/1972 | Hill |
| 3,671,450 A | | 6/1972 | Rauhut et al. |
| 3,728,446 A | | 4/1973 | Roberts et al. |
| 4,008,136 A | * | 2/1977 | Williams ............ B01J 19/122 204/158.2 |
| 4,574,097 A | | 3/1986 | Honeycutt |
| 4,846,165 A | | 7/1989 | Hare et al. |
| 4,891,211 A | | 1/1990 | Winston |
| 4,923,726 A | | 5/1990 | Maruyama et al. |
| 4,992,256 A | | 2/1991 | Skaggs et al. |
| 5,292,362 A | | 3/1994 | Bass et al. |
| 5,516,227 A | | 5/1996 | Kozak et al. |
| 5,611,793 A | | 3/1997 | Wilson et al. |
| 5,658,148 A | | 8/1997 | Neuberger et al. |
| 5,723,148 A | | 3/1998 | Love |
| 5,749,968 A | | 5/1998 | Melanson et al. |
| 5,785,527 A | | 7/1998 | Jensen et al. |
| 5,844,016 A | | 12/1998 | Sawhney et al. |
| 5,858,332 A | | 1/1999 | Jensen et al. |
| 5,922,331 A | | 7/1999 | Mausner |
| 5,977,199 A | | 11/1999 | Xie |
| 6,030,222 A | | 2/2000 | Tarver |
| 6,036,493 A | | 3/2000 | Sharma |
| 6,056,548 A | | 5/2000 | Neuberger et al. |
| 6,084,005 A | | 7/2000 | Fukunishi et al. |
| 6,107,466 A | | 8/2000 | Hasan et al. |
| 6,121,341 A | | 9/2000 | Sawhney et al. |
| 6,149,895 A | | 11/2000 | Kutsch |
| 6,162,055 A | | 12/2000 | Montgomery et al. |
| 6,254,388 B1 | | 7/2001 | Yarborough |
| 6,267,976 B1 | | 7/2001 | Barnhart et al. |
| 6,337,357 B1 | | 1/2002 | Fukunishi et al. |
| 6,343,933 B1 | | 2/2002 | Montgomery et al. |
| 6,361,329 B1 | | 3/2002 | Dekker et al. |
| 6,365,134 B1 | | 4/2002 | Orlowski et al. |
| 6,387,353 B1 | | 5/2002 | Jensen et al. |
| 6,391,283 B1 | | 5/2002 | Jensen et al. |
| 6,420,455 B1 | * | 7/2002 | Landgrebe ............ A45C 11/005 523/122 |
| 6,423,697 B1 | | 7/2002 | Friedman |
| 6,440,396 B1 | | 8/2002 | McLaughlin |
| 6,444,725 B1 | | 9/2002 | Trom et al. |
| 6,475,497 B1 | | 11/2002 | Rajaiah et al. |
| 6,485,709 B2 | | 11/2002 | Banerjee et al. |
| 6,488,914 B2 | | 12/2002 | Montgomery |
| 6,514,543 B2 | | 2/2003 | Montgomery |
| 6,528,555 B1 | | 3/2003 | Nikutowski et al. |
| 6,536,628 B2 | | 3/2003 | Montgomery |
| 6,541,460 B2 | | 4/2003 | Petito |
| 6,558,653 B2 | | 5/2003 | Andersen et al. |
| 6,846,182 B1 | | 1/2005 | Sibner |
| 6,905,672 B2 | | 6/2005 | Rajaiah et al. |
| 6,960,079 B2 | | 11/2005 | Brennan et al. |
| 7,066,941 B2 | | 6/2006 | Perricone |
| 7,081,128 B2 | | 7/2006 | Hart et al. |
| 7,083,610 B1 | | 8/2006 | Murray et al. |
| 7,114,953 B1 | | 10/2006 | Wagner |
| 7,220,438 B2 | | 5/2007 | Quintanilla Almagro et al. |
| 7,314,470 B2 | | 1/2008 | Malodobry |
| 7,354,448 B2 | | 4/2008 | Altshuler et al. |
| 8,075,875 B2 | | 12/2011 | Piergallini et al. |
| 8,182,473 B2 | | 5/2012 | Altshuler et al. |
| 8,334,328 B2 | | 12/2012 | Marmarinos et al. |
| 8,414,911 B2 | | 4/2013 | Mattson |
| 8,632,822 B2 | | 1/2014 | Piergallini et al. |
| 8,637,086 B2 | | 1/2014 | Piergallini et al. |
| 8,658,219 B2 | | 2/2014 | Piergallini et al. |
| 8,685,466 B2 | | 4/2014 | Piergallini et al. |
| 8,911,791 B2 | | 12/2014 | Piergallini et al. |
| 8,974,833 B2 | | 3/2015 | Piergallini et al. |
| 8,986,719 B2 | | 3/2015 | Piergallini et al. |
| 8,986,745 B2 | | 3/2015 | Piergallini et al. |
| 8,986,746 B2 | | 3/2015 | Piergallini et al. |
| 9,375,446 B2 | | 6/2016 | Piergallini et al. |
| 2001/0022970 A1 | | 9/2001 | Dees et al. |
| 2003/0133940 A1 | | 7/2003 | Dees et al. |
| 2003/0198605 A1 | | 10/2003 | Montgomery |
| 2004/0026569 A1 | | 2/2004 | Preston |
| 2004/0136971 A1 | | 7/2004 | Scharp et al. |
| 2004/0191330 A1 | | 9/2004 | Keefe et al. |
| 2005/0020696 A1 | | 1/2005 | Montgomery et al. |
| 2005/0026298 A1 | | 2/2005 | Bickett et al. |
| 2005/0042712 A1 | | 2/2005 | Huth et al. |
| 2005/0049228 A1 | | 3/2005 | Albrecht et al. |
| 2005/0059731 A1 | | 3/2005 | Albrecht et al. |
| 2005/0098766 A1 | | 5/2005 | Watson et al. |
| 2005/0123588 A1 | | 6/2005 | Zhu et al. |
| 2006/0099155 A1 | | 5/2006 | MacDonald et al. |
| 2006/0198796 A1 | | 9/2006 | Giniger et al. |
| 2006/0217690 A1 | | 9/2006 | Bastin et al. |
| 2006/0251687 A1 | | 11/2006 | Lapidot et al. |
| 2006/0287211 A1 | | 12/2006 | Barbizan et al. |
| 2007/0092469 A1 | | 4/2007 | Jacobs |
| 2007/0128132 A1 | | 6/2007 | Piergallini et al. |
| 2007/0142762 A1 | | 6/2007 | Kaplan et al. |
| 2007/0166369 A1 | | 7/2007 | Neuberger et al. |
| 2007/0191249 A1 | | 8/2007 | Lant |
| 2007/0244195 A1 | | 10/2007 | Burkhart et al. |
| 2008/0058689 A1 | | 3/2008 | Holloway et al. |
| 2008/0108681 A1 | | 5/2008 | Scimeca et al. |
| 2008/0113037 A1 | | 5/2008 | Green et al. |
| 2008/0138289 A1 | | 6/2008 | Goronkin et al. |
| 2008/0206159 A1 | | 8/2008 | Tamarkin et al. |
| 2008/0255498 A1 | | 10/2008 | Houle |
| 2008/0305101 A1 | | 12/2008 | Ruoslahti et al. |
| 2009/0238778 A1 | | 9/2009 | Mordas et al. |
| 2010/0227799 A1 | | 9/2010 | Trudel |
| 2010/0255045 A1 | | 10/2010 | Eymard Du Vernet |
| 2010/0266989 A1 | | 10/2010 | Piergallini et al. |
| 2011/0027753 A1 | | 2/2011 | Maurat et al. |
| 2011/0171310 A1 | * | 7/2011 | Gousse .................. A61L 27/20 424/488 |

(56) References Cited

U.S. PATENT DOCUMENTS

| | | |
|---|---|---|
| 2011/0218482 A1 | 9/2011 | Piergallini et al. |
| 2011/0224599 A1 | 9/2011 | Piergallini et al. |
| 2011/0245748 A1 | 10/2011 | Rinke |
| 2012/0095455 A1 | 4/2012 | Rodmond et al. |
| 2012/0171641 A1 | 7/2012 | Piergallini et al. |
| 2013/0122467 A1 | 5/2013 | Piergallini et al. |
| 2013/0281913 A1 | 10/2013 | Piergallini et al. |
| 2014/0105832 A1 | 4/2014 | Loupis et al. |
| 2014/0276354 A1 | 9/2014 | Piergallini et al. |
| 2014/0303547 A1 | 10/2014 | Loupis et al. |
| 2015/0065453 A1 | 3/2015 | Piergallini et al. |
| 2015/0119788 A1 | 4/2015 | Loupis et al. |
| 2015/0290103 A1 | 10/2015 | Piergallini et al. |
| 2015/0290320 A1 | 10/2015 | Piergallini et al. |
| 2015/0306131 A1 | 10/2015 | Piergallini et al. |

FOREIGN PATENT DOCUMENTS

| | | |
|---|---|---|
| CA | 2457590 | 8/2002 |
| CA | 2551613 | 12/2005 |
| CA | 2580381 | 1/2006 |
| CA | 2632187 | 5/2008 |
| CA | 2677468 | 11/2011 |
| CA | 2797867 | 11/2011 |
| CA | 2809405 | 1/2012 |
| CN | 101594904 | 12/2009 |
| CN | 102133208 A | 7/2011 |
| DE | 2935450 A1 | 3/1981 |
| EP | 0356868 | 3/1990 |
| EP | 0380157 | 8/1990 |
| EP | 0704539 | 4/1996 |
| EP | 1235543 | 9/2002 |
| EP | 1235544 | 9/2002 |
| EP | 1749532 | 2/2007 |
| EP | 1779891 | 5/2007 |
| EP | 1951184 | 8/2008 |
| EP | 2338465 | 6/2011 |
| JP | 01-279838 | 10/1989 |
| JP | 2002-233612 | 9/1990 |
| JP | H03169805 | 7/1991 |
| JP | H10182390 | 7/1998 |
| JP | H10330235 | 12/1998 |
| JP | H092925 | 1/1999 |
| JP | 2000-053550 | 2/2000 |
| JP | 2001-511137 | 8/2001 |
| JP | 2002-502864 | 1/2002 |
| JP | 2002-226349 | 8/2002 |
| JP | 2002-293747 | 10/2002 |
| JP | 2003-339875 | 12/2003 |
| JP | 2004-219756 | 2/2009 |
| KR | 10-20070017292 A | 2/2007 |
| SG | 194945 | 11/2012 |
| WO | WO-1981000513 | 3/1981 |
| WO | WO-1990009779 | 9/1990 |
| WO | WO-1991002530 | 7/1991 |
| WO | WO-1997021420 | 6/1997 |
| WO | WO-1998010738 | 3/1998 |
| WO | WO-1998011827 | 3/1998 |
| WO | WO-1998023219 | 6/1998 |
| WO | WO-1998030169 | 7/1998 |
| WO | WO-1998033761 | 8/1998 |
| WO | WO-1998036700 | 8/1998 |
| WO | WO-1999039238 | 8/1999 |
| WO | WO-1999040870 | 8/1999 |
| WO | WO-1999049823 | 10/1999 |
| WO | WO-1999063900 | 12/1999 |
| WO | WO-2000040266 | 7/2000 |
| WO | WO-2001000190 | 1/2001 |
| WO | WO 01/12181 * | 2/2001 |
| WO | WO-2001012181 | 2/2001 |
| WO | WO-2002022097 | 3/2002 |
| WO | WO-2002087642 | 11/2002 |
| WO | WO-2003000215 | 1/2003 |
| WO | WO-2003017824 | 3/2003 |
| WO | WO-2003061696 | 7/2003 |
| WO | WO-2003086215 | 10/2003 |
| WO | WO-2003099247 | 12/2003 |
| WO | WO-2004028498 | 4/2004 |
| WO | WO-2004073540 | 9/2004 |
| WO | WO-2004081222 | 9/2004 |
| WO | WO-2005009604 | 2/2005 |
| WO | WO-2005051305 | 6/2005 |
| WO | WO-2006014597 | 2/2006 |
| WO | WO-2006032847 | 3/2006 |
| WO | WO-2006047868 | 5/2006 |
| WO | WO-2006072243 | 7/2006 |
| WO | WO-2006125650 | 11/2006 |
| WO | WO-2006135344 | 12/2006 |
| WO | WO-2007025244 | 3/2007 |
| WO | WO-2007080453 | 7/2007 |
| WO | WO-2007087259 A2 | 8/2007 |
| WO | WO-2007127172 | 11/2007 |
| WO | WO-2008011707 | 1/2008 |
| WO | WO-2008013962 | 1/2008 |
| WO | WO-2008052081 | 5/2008 |
| WO | WO-2008096182 | 8/2008 |
| WO | WO-2009089346 | 7/2009 |
| WO | WO-2010051636 | 5/2010 |
| WO | WO-2010051641 | 5/2010 |
| WO | WO-2010070292 | 6/2010 |
| WO | WO 2010/151563 * | 12/2010 |
| WO | WO-2011006263 | 1/2011 |
| WO | WO-2011058448 | 5/2011 |
| WO | WO-2011134087 | 11/2011 |
| WO | WO-2012011875 | 1/2012 |
| WO | WO-2012072980 | 6/2012 |
| WO | WO-2012126120 | 9/2012 |
| WO | WO-2013155620 | 10/2013 |
| WO | WO-2014040176 | 3/2014 |
| WO | WO-2014040177 | 3/2014 |
| WO | WO-2014042936 | 3/2014 |
| WO | WO-2014138930 | 9/2014 |

OTHER PUBLICATIONS

Chen et al., "Study of the Chemiluminescent Characteristics of Some Xanthone Dyes," Analytica Chimica Acta, 292(1-2):159-167 (1994).

Mintel, "Teens Braces Cleaner," http://gnpd.com, Jan. 2004 (2 pages).

Nolan et al, "The efficacy of topical hyaluronic acid in the management of oral lichen planus," Journal of Oral Pathology and Medicine, 38(3):299-303 (2009).

Tao, et al, "Gastrointestinal Patch Systems for Oral Drug Delivery", Drug Discovery Today, vol. 10, No. 13, Jul. 2005, pp. 909-915.

Rodgers, Fluorescence Polarization Standards for High-Throughput Screening and Imaging 2002, BioTechniques 32: (5 pages).

Slyusareva, et al. "Spectral and Photophysical Properties of Flourone Dyes in Bio-Related Films and Methanol", Journal of Photochemistry and Photobiology A; Chemistry 208 (2009), pp. 131-140.

Tsuboi et al., "Photoluminescence Properties of Fluorone Dyes in Bio-Related Films at Low Temperatures" Journal of Photochemistry and Photobiology A; Chemistry; 222 (2011) pp. 336-342.

Alster, et al., "Photodynamic therapy: practical cosmetic applications," Journal of Drugs in Dermatology, 5(8):764-768 (2006).

Antunes, et al., "Evaluation of the clastogenicity and anticlastongenicity of the carotenoid bixin in human lymphocyte cultures," Mutation Research, 585(1-2):113-9 (2005).

Ariizumi et al., "Clinical evaluation of a topical applicant TSG-88 for periodontal disease," Dental Drug Therapy, 10(2):157-168 (1998) (English Abstract included).

Berneburg, et al., "Phototherapy with narrowband UVB," Acta Dermato-Venereologica, 85:1-11 (2005).

Colman, et al., "The healing of wounds in the skin of piglets treated with benzoyl peroxide," The Journal of Dermatologic Surgery and Oncology, 4(9):705-707 (1978).

Darzynkiewicz, et al., "Photosensitizing effects of the tricyclic heteroaromatic cationic dyes pyronin Y and toluidine blue O (tolonium chloride)," Cancer Research, 48(5):1295-1299 (1988).

(56) References Cited

OTHER PUBLICATIONS

De, et al., "Environmental effects on the aggregation of some xanthene dyes used in lasers," Spectrochimica Acta Part A: Molecular and Biomolecular Spectroscopy, 61(8):1821-1833 (2005).
Decraene et al., "Cellulose acetate containing toluidine blue and rose bengal is an effective antimicrobial coating when exposed to white light," Applied and Env. Microbiology, 72:6(4436-4439) (Jun. 2006).
Eurasian Search Report, Serial No. 201291068, dated May 29, 2013 with English translation (3 pages).
European Search Report and Written Opinion, Application No. EP11161795, dated May 23, 2011 (6 pages).
FDA, Color Additive Status List, http://www.cfsanJda.gov/-dms/opa-appc.html, downloaded Jun. 18, 2008 (13 pages).
FDA, Product Classification Database Search, http://www.accessdata.fda.gov/scripts/cdrh/cfdocs/cfpcd/classificiation/c.f?ID-3964, Device: Eosin y: database, downloaded Jun. 18, 2008 (2 pages).
Fisher Scientific, "Material Safety Data Sheet: Sodium acetate buffer," https://fscimagef.fishersci.com/msds/91502.htm (ACC #91502) (Apr. 13, 2000) (5 pages).
Goldberg, "Photodynamic therapy in skin rejuvenation," Clinics in Dermatology, 26(6):608-613 (2008).
Jankowski, et al., "The action of photosensitizers and serum in a bactericidal process. II. The effects of dyes: hypericin, eosin Y and saphranine O," Polish Journal of Microbiology, 54(4):323-230 (2005).
Kelly, et al., "Combined photodynamic and photothermal induced injury enhances damage to in vivo model blood vessels," Lasers in Surgery and Medicine, 34(5):407-413 (2004).
McCullach, et al., "Photosensitized destruction of Chlorella vulgaris by methylene blue or nuclear fast red combined with hydrogen peroxide under visible light irradiation," Environmental Science and Technology, 40(7):2421-2425 (2006).
Meisel, et al., "Photodynamic therapy for periodontal diseases: State of the art," Journal of Photochemistry and Photobiology B: Biology, 79:159-170 (2005).
Montenegro, et al., "Model studies on the photosensitized isomerication of bixin," Journal of Agriculture and Food Chemistry, 52(2): 367-73 (2004).
Nolan et al., "The efficacy of topical hyaluronic acid in the management of oral lichen planus," Journal of Oral Pathology and Medicine, 38:3:299-303 (2009).
Olympus America Inc., "Special characteristics of common biological stains," http://micro.magnet.fsu.edu/primer/photomicrography/bwstainchart.html, Apr. 30, 2000 (3 pages).
PCT International Preliminary Report on Patentability and Written Opinion for International Serial No. PCT/CA2013/000786, dated Mar. 17, 2015 (15 pages).
PCT International Preliminary Report on Patentability and Written Opinion for International Serial No. PCT/CA2013/000787, dated Mar. 17, 2015 and Nov. 27, 2013 (9 pages).
PCT International Search Report and Written Opinion for International Serial No. PCT/CA2011/050261, dated Aug. 4, 2011 (6 pages).
PCT International Search Report and Written Opinion for International Serial No. PCT/CA2012/050177, dated Jun. 28, 2012 (8 pages).
PCT International Search Report and Written Opinion for International Serial No. PCT/GR2007/000006, dated Oct. 12, 2007 (8 pages).
PCT International Search Report and Written Opinion for International Serial No. PCT/IB2006/004034, dated Sep. 20, 2007 (13 pages).
PCT International Search Report Corrected for International Serial No. PCT/CA2014/000261, dated Jun. 19, 2014 (7 pages).
PCT International Search Report for International Application No. PCT/CA2009/001615, dated Feb. 9, 2010 (9 pages).
PCT International Search Report for International Application No. PCT/CA2013/000395, dated Jul. 15, 2013 (12 pages).
Publication date of following document established by Internet Archive Wayback Machine (3 pages) <URL: <http://web.archive.org/web/20090208211504/http://en.wikipedia.org/wiki/Eosin Aug. 2, 2009.
Resources: Fluorochrome absorption emission wavelengths [Online] XP002449595 Retrieved from the Internet: URL: http://www.sciencegateway.org/resources/fae 1.htm>[retrieved on Sep. 6, 2007] see p. 2: Rhodamine WT emission nm 555 p. 2 (12 pages).
Rodgers, "Fluorescence polarization standards for high-throughput screening and imaging," Bio Techniques, 32:34-42 (2002).
Roy et al., "Dermal wound healing is subject to redox control," Molecular Therapy, 13(1):211-220 (2006).
Sezer, et al., "Topical drug delivery using chitosan nano- and microparticles," Expert Opinion in Drug Delivery, Informa UK, 9(9):1129-1146 (2012).
Steinberg, et al., "Genetic and physiological effects of noncoherent visible light combined with hydrogen peroxide on *Streptococcus mutans* in biofilm," Antimicrobial Agents and Chemotherapy, 52(7):2626-2631 (2008).
Subba, et al, "Photocatalytic transformation of dyes and by-products in the presence of hydrogen peroxide," Environmental Technology, 24(8):1025-1030 (2003).
Sun, "Lasers and light amplification in dentistry," retrieved online at http://www.sundds.comllaser/, downloaded Jun. 23, 2005 (14 pages).
Gonzales et al., "Photodynamic inactivation of microorganisms as an innovative approach to kill mucocutaneous and skin microorganisms," Giornale Italiano Di Dermatologia e Venereologia, 145, pp. 477-489 (2010).
"Lins, et al.,"Enhancement of Antimicrobial Action of Photodynamic Therapy in the Presence of Hydrogen Peroxide, "in Microbial Pathogens and Strategies for Combating Them: Science, Technology and Education," Edition: Microbiology Book Series #4, Editor: A. Mendez-Vilas, pp. 367-371 (2013) (acquired from:.
Mintel, "Active Plus Deep Cleaning Tablets," Database GNPD [Online].
Mintel, "Effervescent Tablets," Database GNPD [Online].

* cited by examiner

BIOPHOTONIC MATERIALS AND USES THEREOF

CROSS REFERENCE TO RELATED APPLICATIONS

This application is a United States National Stage Application under 35 U.S.C. § 371 of International Application No. PCT/CA2014/000261, filed Mar. 14, 2014, which is a continuation-in-part of U.S. patent application Ser. No. 14/204,741, filed Mar. 11, 2014, which claims the benefit of U.S. Provisional Patent Application No. 61/786,197, filed Mar. 14, 2013, and U.S. Provisional Patent Application No. 61/873,747, filed Sep. 4, 2013, all of which are hereby incorporated by reference in their entireties. International Application No. PCT/CA2014/000261 was published under PCT Article 21(2) in English.

FIELD OF THE INVENTION

The present disclosure generally relates to biophotonic materials for phototherapy.

BACKGROUND OF THE DISCLOSURE

Phototherapy has recently been recognized as having wide range of applications in both the medical and cosmetic fields including use in surgery, therapy and diagnostics. For example, phototherapy has been used to treat cancers and tumors with lessened invasiveness, to disinfect target sites as an antimicrobial treatment, to promote wound healing, and for facial skin rejuvenation.

Photodynamic therapy is a type of phototherapy involving the application of a photosensitive agent to target tissue then exposing the target tissue to a light source after a determined period of time during which the photosensitizer is absorbed by the target tissue. Such regimens, however, are often associated with undesired side-effects, including systemic or localized toxicity to the patient or damage to non-targeted tissue. Moreover, such existing regimens often demonstrate low therapeutic efficacy due to, for example, the poor selectivity of the photosensitive agents into the target tissues.

Therefore, it is an object of the present disclosure to provide new and improved compositions and methods useful in phototherapy.

SUMMARY OF THE DISCLOSURE

The present disclosure provides topical biophotonic materials and methods useful in phototherapy.

In particular, the biophotonic materials of the present disclosure include a cohesive matrix, and at least one chromophore, wherein the at least one chromophore can absorb and emit light from within the biophotonic material. In certain embodiments of any of the foregoing or following, the biophotonic material is an elastic material.

From another aspect, there is provided a topical biophotonic material comprising: a cohesive matrix, and at least one chromophore which can absorb and emit light from within the biophotonic material, wherein the topical biophotonic material is a peelable film.

From another aspect, there is provided a topical biophotonic material comprising: a cohesive matrix, and at least one chromophore which can absorb and emit light from within the biophotonic material, wherein the topical biophotonic material is elastic.

From yet another aspect, there is provided a topical biophotonic material comprising: a cohesive matrix, and at least one chromophore which can absorb and emit light from within the biophotonic material, wherein the topical biophotonic material is rigid.

From another aspect, there is provided a topical biophotonic material comprising: a cohesive matrix, and at least one chromophore which can absorb and emit light from within the biophotonic material, wherein a tear and/or a tensile strength of the topical biophotonic material is greater than an adhesive strength of the topical biophotonic material to a surface to which it is applied.

From a yet further aspect, there is provided a topical biophotonic material comprising: a cohesive matrix, and at least one chromophore which can absorb and emit light from within the biophotonic material, wherein the topical biophotonic material has a well-defined shape under steady state conditions.

From another aspect, there is provided a topical biophotonic material comprising: a cohesive matrix, and at least one chromophore which can absorb and emit light from within the biophotonic material, wherein the topical biophotonic material is a mask or a dressing. In certain embodiments, the mask and/or the dressing has a pre-formed configuration. In certain embodiments, the mask and/or the dressing is elastic. In certain embodiments, the mask and/or the dressing is rigid.

From another aspect, there is provided a biophotonic material comprising: a cohesive matrix, and at least one chromophore which can absorb and emit light from within the biophotonic material, wherein the biophotonic material has a pre-formed configuration which is a shape and/or a size corresponding with a shape and/or a size of a light source or lamp to which the biophotonic material can be attached.

In certain embodiments of the above aspects, the biophotonic material is a peelable film. In some embodiments, the biophotonic material is rigid.

In certain embodiments of any of the foregoing or following, the biophotonic material has a tear and/or a tensile strength greater than an adhesive strength of the biophotonic material to a surface to which it is applied. The adhesive strength may comprise a force required to overcome static friction.

In certain embodiments of any of the foregoing or following, the biophotonic material is at least substantially translucent. The biophotonic material may be transparent. In some embodiments, the biophotonic material has a translucency of at least about 40%, about 50%, about 60%, about 70%, or about 80% in a visible range. Preferably, the light transmission through the material is measured in the absence of the at least one chromophore.

In certain embodiments of any of the foregoing or following, the biophotonic material has a thickness of about 0.1 mm to about 50 mm, about 0.5 mm to about 20 mm, or about 1 mm to about 10 mm.

In certain embodiments of any of the foregoing or following, the biophotonic material has a pre-formed configuration. In some embodiments, the pre-formed configuration is a shape and/or a size corresponding with a shape and/or a size of a body part to which the biophotonic material can be applied. In some embodiments, the body part to which the material is applied is a head, scalp, forehead, nose, cheeks, ears, lip, face, neck, shoulder, arm pit, arm, elbow, hand, finger, abdomen, chest, stomach, back, sacrum, buttocks, genitals, legs, knee, feet, nails, hair, toes, or bony prominences, or combinations thereof.

In certain embodiments of any of the foregoing or following, the biophotonic material is a mask. In some embodiments, the mask is a face mask having at least one opening for the eyes, nose or mouth. In certain embodiments, the mask is disposable. The mask may also be reusable. The chromophore may at least substantially photobleach after a single use or single light illumination.

In certain embodiments of any of the foregoing or following, the biophotonic material has a pre-formed configuration and the pre-formed configuration is a shape and/or a size corresponding with a shape and/or a size of a light source or lamp to which the biophotonic material can be attached.

In certain embodiments of any of the foregoing or following, the biophotonic material can be removed without leaving substantially any residue on a surface to which the biophotonic material is applied.

In certain embodiments of any of the foregoing or following, the at least one chromophore included in the biophotonic material is a fluorophore. In certain embodiments, the chromophore can absorb and/or emit light within the visible range. The chromophore may be water soluble. In certain embodiments, the chromophore can emit light from around 500 nm to about 700 nm. In some embodiments, the chromophore or the fluorophore is a xanthene dye. The xanthene dye may be selected from Eosin Y, Erythrosine B, Fluorescein, Rose Bengal and Phloxine B. In some embodiments, the chromophore is included in the cohesive matrix. In certain embodiments of any of the foregoing or following, the cohesive matrix is in particulate form.

In certain embodiments of any of the foregoing or following, the cohesive matrix of the biophotonic material comprises at least one polymer. In some embodiments, the polymer is selected from a cross-linked polyacrylic polymer, a hyaluronate, a hydrated polymer, a hydrophilic polymer and a liposoluble polymer. In some embodiments, the cohesive matrix comprises sodium hyaluronate. In some embodiments, sodium hyaluronate is present in an amount of about 2% to about 8%.

In certain embodiments, the cohesive matrix is a liposoluble polymer, such as silicone. The chromophore(s) may be water soluble and be within an aqueous phase within the liposoluble polymer. In this case, the biophotonic material comprises an aqueous phase containing the chromophore within the liposoluble polymer phase. The aqueous phase may comprise about 2 wt % to about 40 wt % of the liposoluble polymer phase. The aqueous phase may be a liquid or a gel. The biophotonic material may further comprise a stabilizing agent such as CMC or gelatin.

In certain embodiments, the cohesive matrix comprises gelatin or chitosan. In certain embodiments, the biophotonic material further comprises an oxygen-rich compound which may be selected from hydrogen peroxide, carbamide peroxide and benzoyl peroxide.

In some embodiments, the chromophore is included in a carrier medium which can form a cohesive matrix. In some embodiments, the chromophore can absorb and emit light within the cohesive matrix when illuminated with light. In some embodiments, the carrier medium is at least one polymer or a polymer pre-cursor which can form the cohesive matrix by polymerizing, cross-linking or drying.

From another aspect, there is provided a topical biophotonic material comprising a water soluble chromophore within an aqueous cohesive matrix, and wherein the aqueous cohesive matrix is dispersed within a liposoluble polymer. In certain embodiments, the liposoluble polymer is silicone. The aqueous phase may be a liquid or a gel. In certain embodiments, the aqueous cohesive matrix may be gelatin, water or carboxymethylcellulose. The chromophore may comprise a fluorophore, such as a xanthene dye selected from Eosin Y, Fluorescein, Erythrosine, Phloxine B and Rose Bengal.

The aqueous phase may comprise about 2 wt % to about 40 wt % of the liposoluble polymer phase. In certain embodiments, the topical biophotonic material may be used to treat wounds, or to treat or prevent scarring.

The biophotonic material of any aspects and embodiments of the disclosure may be used as a mask, dressing or filter. The biophotonic material of any aspects or embodiments of the disclosure may also be used for cosmetic or medical treatment of tissue. In some embodiments, the cosmetic treatment is skin rejuvenation and conditioning, and the medical treatment is wound healing, periodontal treatment or acne treatment or treatment of other skin conditions including acne, eczema, psoriasis or dermatitis. In some aspects, the topical biophotonic material is used for modulating inflammation, or for promoting angiogenesis.

The present disclosure also provides containers comprising the biophotonic material or precursor material according to various embodiments of the disclosure. In some embodiments, the container comprises a sealed chamber for holding a biophotonic material, and an outlet in communication with the chamber for discharging the biophotonic material from the container, wherein the biophotonic material comprises at least one chromophore in a carrier medium which can form a cohesive matrix after being discharged from the sealed chamber. In some embodiments, the container is a spray can. The container may be opaque.

The present disclosure also provides kits for preparing or providing the biophotonic material or precursor according to various embodiments of the disclosure. In some embodiments, the kit comprises a first container comprising a first chromophore; and a second component comprising a thickening agent, wherein the thickening agent can form a cohesive matrix when mixed with the first component. In some embodiments, the second container may comprise an oxygen-rich compound.

The present disclosure also provides methods for biophotonic treatment comprising applying the topical biophotonic material of the disclosure to a target tissue and illuminating the material with light.

From one aspect, there is provided a method for biophotonic treatment of a skin disorder wherein the method comprises placing a biophotonic material on or over a target skin tissue, wherein the biophotonic material is elastic and comprises at least one chromophore and a cohesive matrix; and illuminating said biophotonic material with light having a wavelength that overlaps with an absorption spectrum of the at least one chromophore; wherein said biophotonic material emits fluorescence at a wavelength and intensity that promotes healing of said skin disorder. The skin disorder may be selected from acne, eczema, psoriasis or dermatitis.

From another aspect, there is provided a method for biophotonic treatment of a skin disorder comprising: placing a topical biophotonic material on or over a target skin tissue, wherein the biophotonic material comprises at least one chromophore and a cohesive matrix, and wherein a tear and/or tensile strength of the topical biophotonic material is greater than an adhesive strength of the topical biophotonic material to a surface to which it applied; and illuminating said topical biophotonic material with light having a wavelength that overlaps with an absorption spectrum of the at least one chromophore; wherein said biophotonic material emits fluorescence at a wavelength and intensity that promotes healing of said skin disorder.

From another aspect, there is provided a method for biophotonic treatment of acne comprising: placing a topical biophotonic material on or over a target skin tissue, wherein the topical biophotonic material is elastic and comprises at least one chromophore and a cohesive matrix; and illuminating said biophotonic material with light having a wavelength that overlaps with an absorption spectrum of the at least one chromophore; wherein said topical biophotonic material emits fluorescence at a wavelength and intensity that treats the acne.

From another aspect, there is provided a method for biophotonic treatment of acne comprising: placing a topical biophotonic material on or over a target skin tissue, wherein the topical biophotonic material comprises at least one chromophore and a cohesive matrix, and wherein a tear and/or tensile strength of the topical biophotonic material is greater than an adhesive strength of the topical biophotonic material to a surface to which it is applied; and illuminating said biophotonic material with light having a wavelength that overlaps with an absorption spectrum of the at least one chromophore; wherein said topical biophotonic material emits fluorescence at a wavelength and intensity that treats the acne.

From another aspect, there is provided a method for promoting wound healing comprising: placing a topical biophotonic material over or within a wound, wherein the topical biophotonic material is elastic and comprises at least one chromophore and a cohesive matrix; and illuminating said biophotonic material with light having a wavelength that overlaps with an absorption spectrum of the at least one chromophore; wherein said topical biophotonic material emits fluorescence at a wavelength and intensity that promotes wound healing.

A method for promoting wound healing comprising: placing a topical biophotonic material over or within a wound, wherein the topical biophotonic material comprises at least one chromophore and a cohesive matrix; and wherein a tear and/or tensile strength of the topical biophotonic material is greater than an adhesive strength of the topical biophotonic material to a surface to which it is applied; and illuminating said biophotonic material with light having a wavelength that overlaps with an absorption spectrum of the at least one chromophore; wherein said topical biophotonic material emits fluorescence at a wavelength and intensity that promotes wound healing.

From another aspect, there is provided a method for promoting skin rejuvenation comprising: placing a topical biophotonic material on or over a target skin tissue, wherein the topical biophotonic material is elastic and comprises at least one chromophore and a cohesive matrix; and illuminating said biophotonic material with light having a wavelength that overlaps with an absorption spectrum of the at least one chromophore; wherein said topical biophotonic material emits fluorescence at a wavelength and intensity that promotes skin rejuvenation.

From another aspect, there is provided a method for promoting skin rejuvenation comprising: placing a topical biophotonic material on or over a target skin tissue, wherein the topical biophotonic material comprises at least one chromophore and a cohesive matrix; and wherein a tear and/or tensile strength of the topical biophotonic material is greater than an adhesive strength of the topical biophotonic material to a surface to which it is applied; and illuminating said biophotonic material with light having a wavelength that overlaps with an absorption spectrum of the at least one chromophore; wherein said topical biophotonic material emits fluorescence at a wavelength and intensity that promotes skin rejuvenation.

In certain embodiments, the biophotonic material is removed after illumination. In certain embodiments, the biophotonic material is peelable and is peeled off after illumination. In certain other embodiments, the biophotonic material is not peelable but can be removed in one or more pieces. The biophotonic material may be a mask or a dressing such a face mask or a wound dressing.

From another aspect, there is provided a method for promoting skin rejuvenation comprising: placing a topical biophotonic material which is a mask on or over a target skin tissue, wherein the topical biophotonic material comprises at least one chromophore and a cohesive matrix; and illuminating said biophotonic material with light having a wavelength that overlaps with an absorption spectrum of the at least one chromophore; wherein said topical biophotonic material emits fluorescence at a wavelength and intensity that promotes skin rejuvenation.

In certain embodiments, the mask is a face mask having at least one opening for the eyes, nose or mouth. The mask may be disposable or reusable.

From another aspect, there is provided a method for promoting wound healing comprising: placing a topical biophotonic material which is a dressing over or within a wound, wherein the topical biophotonic material comprises at least one chromophore and a cohesive matrix; and illuminating said biophotonic material with light having a wavelength that overlaps with an absorption spectrum of the at least one chromophore; wherein said topical biophotonic material emits fluorescence at a wavelength and intensity that promotes wound healing.

From another aspect, there is provided a method for preventing or treating scarring comprising: placing a topical biophotonic material which is a membrane over or within a wound, wherein the topical biophotonic material comprises at least one chromophore and a cohesive matrix; and illuminating said biophotonic material with light having a wavelength that overlaps with an absorption spectrum of the at least one chromophore; wherein said topical biophotonic material emits fluorescence at a wavelength and intensity that promotes wound healing.

In certain embodiments, the biophotonic material is left in place after illumination for re-illumination. In certain embodiments, the chromophore at least partially photobleaches after illumination. In certain embodiments, the biophotonic material is illuminated until the chromophore is at least partially photobleached.

In certain embodiments, the topical biophotonic material is illuminated with visible light. In certain embodiments of any of the foregoing or following, the at least one chromophore included in the biophotonic material is a fluorophore. In certain embodiments, the chromophore can absorb and/or emit light within the visible range. The chromophore may be water soluble. In certain embodiments, the chromophore can emit light from around 500 nm to about 700 nm. In some embodiments, the chromophore or the fluorophore is a xanthene dye. The xanthene dye may be selected from Eosin Y, Erythrosine B, Fluorescein, Rose Bengal and Phloxine B. In some embodiments, the chromophore is included in the cohesive matrix.

In certain embodiments of any of the foregoing or following, the biophotonic material is at least substantially translucent. The biophotonic material may be transparent. In some embodiments, the biophotonic material has a translucency of at least about 40%, about 50%, about 60%, about 70%, or about 80% in a visible range. Preferably, the light transmission through the material is measured in the absence of the at least one chromophore. In certain embodiments of any of the foregoing or following, the biophotonic material has a thickness of about 0.1 mm to about 50 mm, about 0.5 mm to about 20 mm, or about 1 mm to about 10 mm.

BRIEF DESCRIPTION OF THE DRAWINGS

Further aspects and advantages of the present invention will become better understood with reference to the description in association with the following in which.

DETAILED DESCRIPTION (1) Overview

Figure 1:
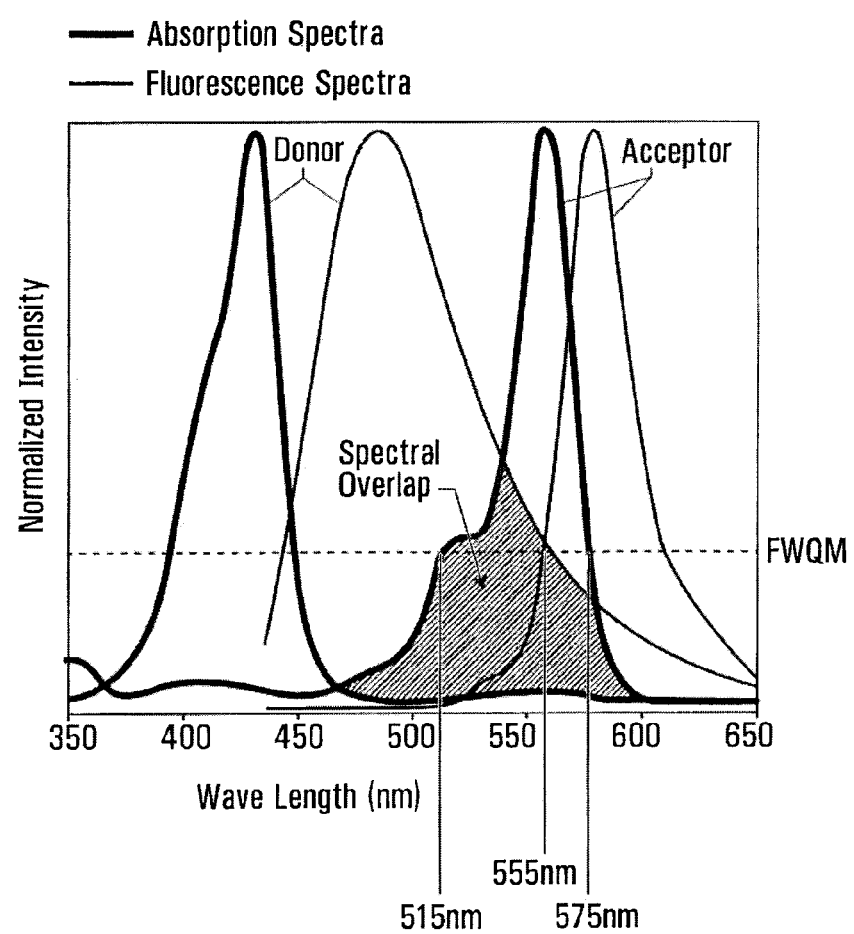
FIG. 1 illustrates the absorption and emission spectra of donor and acceptor chromophores. The spectral overlap between the absorption spectrum of the acceptor chromophore and the emission spectrum of the donor chromophore is also shown.

The present disclosure provides biophotonic materials and uses thereof. Biophotonic therapy using these materials would not involve substantial direct contact of a photosensitive agent (or chromophore) with the therapeutic target, which includes, but is not limited to, skin, mucous membranes, wounds, hair and nails. Therefore, undesired side effects caused by such direct contact may be reduced, minimized, or prevented. Furthermore, in certain embodiments, phototherapy using the biophotonic materials of the present disclosure will for instance rejuvenate the skin by, e.g., promoting collagen synthesis, promote wound healing, treat skin conditions such as acne, and treat periodontitis.

(2) Definitions

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Biophotonic" means the generation, manipulation, detection and application of photons in a biologically relevant context. In other words, biophotonic compositions and materials exert their physiological effects primarily due to the generation and manipulation of photons.

"Biophotonic material" is a material which may be activated by light to produce photons for biologically relevant applications. Biophotonic materials, as referred to herein, may be cohesive gels, semi-solids or solids. The biophotonic material can be in the form of, including, but not limited to, a film or the like, for uses such as a mask, a dressing or a light attachment. The biophotonic material can be a composite and include fibres, particulates, ribs, supporting structures, networks, non-biophotonic layers or biophotonic layers with the same or different compositions.

"Cohesive matrix" refers to a medium which is, or which can form, a self-supporting material e.g. a material with a defined shape under steady state conditions. This may be due to internal attractive forces. The property of cohesion in a material can allow the material to be handled without tearing.

"Topical application" or "topical uses" means application to body surfaces, such as the skin, mucous membranes, vagina, oral cavity, internal surgical wound sites, and the like.

Terms "chromophore" and "photoactivator" are used herein interchangeably. A chromophore means a chemical compound, when contacted by light irradiation, is capable of absorbing the light. The chromophore readily undergoes photoexcitation and can transfer its energy to other molecules or emit it as light (fluorescence).

"Photobleaching" or "photobleaches" means the photochemical destruction of a chromophore. A chromophore may fully or partially photobleach.

The term "actinic light" is intended to mean light energy emitted from a specific light source (e.g. lamp, LED, or laser) and capable of being absorbed by matter (e.g. the chromophore or photoactivator). In a preferred embodiment, the actinic light is visible light.

A "peel-off" or "peelable" film, membrane or matrix is one that can be mechanically removed, such as by hand, after application. It can be removed as a single piece, or as a small number of large pieces.

"Skin rejuvenation" means a process of reducing, diminishing, retarding or reversing one or more signs of skin aging or generally improving the condition of skin. For instance, increasing luminosity of the skin, reducing pore size, reducing fine lines or wrinkles, improving thin and transparent skin, improving firmness, improving sagging skin (such as that produced by bone loss), improving dry skin (which might itch), reducing or reversing freckles, age spots, spider veins, rough and leathery skin, fine wrinkles that disappear when stretched, reducing loose skin, or improving a blotchy complexion. According to the present disclosure, one or more of the above conditions may be improved or one or more signs of aging may be reduced, diminished, retarded or even reversed by certain embodiments of the compositions, methods and uses of the present disclosure.

"Wound" means an injury to any tissue, including for example, acute, subacute, delayed or difficult to heal wounds, and chronic wounds. Examples of wounds may include both open and closed wounds. Wounds include, for example, amputations, burns, incisions, excisions, lesions, lacerations, abrasions, puncture or penetrating wounds, surgical wounds, amputations, contusions, hematomas, crushing injuries, ulcers (such as for example pressure, diabetic, venous or arterial), wounds caused by periodontitis (inflammation of the periodontium).

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

(3) Biophotonic Materials

The present disclosure provides, in a broad sense, topical biophotonic materials which are cohesive and methods of using the biophotonic materials. Biophotonic materials can be, in a broad sense, activated by light (e.g., photons) of specific wavelength. A biophotonic material according to various embodiments of the present disclosure contains a cohesive matrix and at least one chromophore in or on the cohesive matrix which is activated by light and accelerates the dispersion of light energy, which leads to light carrying on a therapeutic effect on its own, and/or to the photochemical activation of other agents contained in the composition (e.g., acceleration in the breakdown process of peroxide (an oxidant) when such compound is present in the composition or in contact with the composition, leading to the formation of oxygen radicals, such as singlet oxygen).

When a chromophore absorbs a photon of a certain wavelength, it becomes excited. This is an unstable condition and the molecule tries to return to the ground state, giving away the excess energy. For some chromophores, it is favorable to emit the excess energy as light when returning to the ground state. This process is called fluorescence. The peak wavelength of the emitted fluorescence is shifted towards longer wavelengths compared to the absorption wavelengths due to loss of energy in the conversion process. This is called the Stokes' shift. In the proper environment (e.g., in a biophotonic material) much of this energy is transferred to the other components of the biophotonic material or to the treatment site directly.

Without being bound to theory, it is thought that fluorescent light emitted by photoactivated chromophores may have therapeutic properties due to its femto-, pico-, or nano-second emission properties which may be recognized by biological cells and tissues, leading to favourable biomodulation. Furthermore, the emitted fluorescent light has a longer wavelength and hence a deeper penetration into the tissue than the activating light. Irradiating tissue with such a broad range of wavelength, including in some embodiments the activating light which passes through the composition, may have different and complementary effects on the cells and tissues. In other words, chromophores are used in the biophotonic materials of the present disclosure for therapeutic effect on tissues. This is a distinct application of these photoactive agents and differs from the use of chromophores as simple stains or as catalysts for photo-polymerization.

The biophotonic materials of the present disclosure may have topical uses such as a mask or a wound dressing, or as an attachment to a light source, as a waveguide or as a light filter. The cohesive nature of these biophotonic materials may provide ease of removal from the site of treatment and hence a faster and less messy treatment. In addition the biophotonic materials can limit the contact between the chromopore and the tissue. These materials may be described based on the components making up the composition. Additionally or alternatively, the compositions of the present disclosure have functional and structural properties and these properties may also be used to define and describe the compositions. Individual components of the biophotonic materials of the present disclosure, including chromophores, thickening agents and other optional ingredients, are detailed below.

The present disclosure also provides a precursor composition to the material described herein, which will become cohesive on drying, heating, light exposure, application to tissue or mixing. The precursor composition comprises at least one chromophore in a carrier medium, or at least one chromophore and a cohesive matrix.

(a) Chromophores

Suitable chromophores can be fluorescent compounds (or stains) (also known as "fluorochromes" or "fluorophores"). Other dye groups or dyes (biological and histological dyes, food colorings, carotenoids, naturally occurring fluorescent and other dyes) can also be used. Suitable photoactivators can be those that are Generally Regarded As Safe (GRAS). Advantageously, photoactivators which are not well tolerated by the skin or other tissues can be included in the biophotonic material of the present disclosure, as in certain embodiments, the photoactivators are encapsulated within the cohesive matrix and may not contact the tissues In certain embodiments, the biophotonic material of the present disclosure comprises a first chromophore which undergoes partial or complete photobleaching upon application of light. In some embodiments, the first chromophore absorbs at a wavelength in the range of the visible spectrum, such as at a wavelength of about 380-800 nm, 380-700, 400-800, or 380-600 nm. In other embodiments, the first chromophore absorbs at a wavelength of about 200-800 nm, 200-700 nm, 200-600 nm or 200-500 nm. In one embodiment, the first chromophore absorbs at a wavelength of about 200-600 nm. In some embodiments, the first chromophore absorbs light at a wavelength of about 200-300 nm, 250-350 nm, 300-400 nm, 350-450 nm, 400-500 nm, 450-650 rim, 600-700 nm, 650-750 nm or 700-800 nm.

It will be appreciated to those skilled in the art that optical properties of a particular chromophore may vary depending on the chromophore's surrounding medium. Therefore, as used herein, a particular chromophore's absorption and/or emission wavelength (or spectrum) corresponds to the wavelengths (or spectrum) measured in a biophotonic material of the present disclosure.

The biophotonic material disclosed herein may include at least one additional chromophore. Combining chromophores may increase photo-absorption by the combined dye molecules and enhance absorption and photo-biomodulation selectivity. This creates multiple possibilities of generating new photosensitive, and/or selective chromophores mixtures. Thus, in certain embodiments, biophotonic materials of the disclosure include more than one chromophore. When such multi-chromophore materials are illuminated with light, energy transfer can occur between the chromophores. This process, known as resonance energy transfer, is a widely prevalent photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. More specifically, for energy transfer to occur, the emission spectrum of the donor chromophore must overlap with the absorption spectrum of the acceptor chromophore (FIG. 1).

Figure 2:
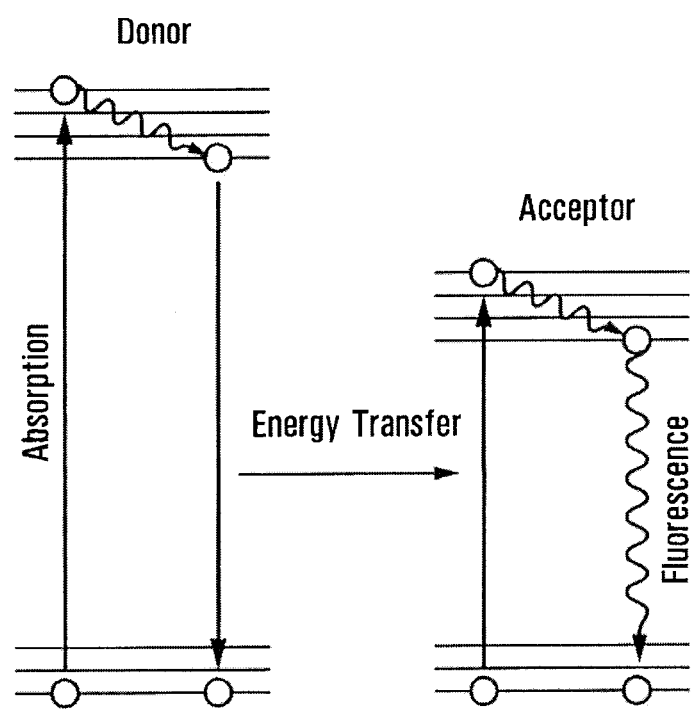
FIG. 2 is a schematic of a Jablonski diagram that illustrates the coupled transitions involved between a donor emission and acceptor absorbance.

Energy transfer manifests itself through decrease or quenching of the donor emission and a reduction of excited state lifetime accompanied also by an increase in acceptor emission intensity. FIG. 2 is a Jablonski diagram that illustrates the coupled transitions involved between a donor emission and acceptor absorbance.

To enhance the energy transfer efficiency, the donor chromophore should have good abilities to absorb photons and emit photons. Furthermore, the more overlap there is between the donor chromophore's emission spectra and the acceptor chromophore's absorption spectra, the better a donor chromophore can transfer energy to the acceptor chromophore.

In certain embodiments, the biophotonic material of the present disclosure further comprises a second chromophore. In some embodiments, the first chromophore has an emission spectrum that overlaps at least about 80%, 50%, 40%, 30%, 20% or 10% with an absorption spectrum of the second chromophore. In one embodiment, the first chromophore has an emission spectrum that overlaps at least about 20% with an absorption spectrum of the second chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore.

% spectral overlap, as used herein, means the % overlap of a donor chromophore's emission wavelength range with an acceptor chromophore's absorption wavelength rage, measured at spectral full width quarter maximum (FWQM). For example, FIG. 1 shows the normalized absorption and emission spectra of donor and acceptor chromophores. The spectral FWQM of the acceptor chromophore's absorption spectrum is from about 60 nm (515 nm to about 575 nm). The overlap of the donor chromophore's spectrum with the absorption spectrum of the acceptor chromophore is about 40 nm (from 515 nm to about 555 nm). Thus, the % overlap can be calculated as 40 nm/60 nm×100=66.6%.

In some embodiments, the second chromophore absorbs at a wavelength in the range of the visible spectrum. In certain embodiments, the second chromophore has an absorption wavelength that is relatively longer than that of the first chromophore within the range of about 50-250, 25-150 or 10-100 nm.

The first chromophore can be present in an amount of about 0.001-40% per weight of the biophotonic material. When present, the second chromophore can be present in an amount of about 0.001-40% per weight of the biophotonic material. In certain embodiments, the first chromophore is present in an amount of about 0.001-3%, 0.001-0.01%, 0.005-0.1%, 0.1-0.5%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the biophotonic material. In certain embodiments, the second chromophore is present in an amount of about 0.001-3%, 0.001-0.01%, 0.005-0.1%, 0.1-0.5%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the biophotonic material. In certain embodiments, the total weight per weight of chromophore or combination of chromophores may be in the amount of about 0.005-1%, 0.05-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.001% per weight of the biophotonic material.

The concentration of the chromophore to be used can be selected based on the desired intensity and duration of the biophotonic activity from the biophotonic material, and on the desired medical or cosmetic effect. For example, some dyes such as xanthene dyes reach a 'saturation concentration' after which further increases in concentration do not provide substantially higher emitted fluorescence. Further increasing the chromophore concentration above the saturation concentration can reduce the amount of activating light passing through the matrix. Therefore, if more fluorescence is required for a certain application than activating light, a high 'saturation' concentration of chromophore can be used. However, if a balance is required between the emitted fluorescence and the activating light, a concentration close to or lower than the saturation concentration can be chosen.

Suitable chromophores that may be used in the biophotonic materials of the present disclosure include, but are not limited to the following:

Chlorophyll Dyes

Exemplary chlorophyll dyes include but are not limited to chlorophyll a; chlorophyll b; chlorophyllin, oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Xanthene Derivatives

Exemplary xanthene dyes include but are not limited to Eosin B (4',5'-dibromo, 2',7'-dinitro-fluorescein, dianion); Eosin Y (2',4',5',7'-tetrabromofluorescein, dianion); Eosin (2',4',5',7'-tetrabromo-fluorescein, dianion); Eosin (2',4',5', 7'-tetrabromo-fluorescein, dianion) methyl ester; Eosin (2', 4',5',7'-tetrabromofluorescein, monoanion) p-isopropylbenzyl ester; Eosin derivative (2',7'-dibromofluorescein, dianion); Eosin derivative (4',5'-dibromo-fluorescein, dianion); Eosin derivative (2',7'-dichloro-fluorescein, dianion); Eosin derivative (4',5'-dichloro-fluorescein, dianion); Eosin derivative (2',7'-diiodo-fluorescein, dianion); Eosin derivative (4',5'-diiodo-fluorescein, dianion); Eosin derivative (tribromo-fluorescein, dianion); Eosin derivative (2',4',5',7'-tetrachloro-fluorescein, dianion); Eosin; Eosin dicetylpyridinium chloride ion pair; Erythrosin B (2',4',5', 7'-tetraiodo-fluorescein, dianion); Erythrosin; Erythrosin dianion; Fluorescein; Fluorescein dianion; Phloxine B (2', 4',5',7'-tetrabromo-3,4,5,6-tetrachloro-fluorescein, dianion); Rose Bengal (3,4,5,6-tetrachloro-2',4',5',7'-tetraiodofluorescein, dianion); Pyronin G, Pyronin J, Pyronin Y; Rhodamine dyes such as rhodamines including 4,5-dibromo-rhodamine methyl ester; 4,5-dibromo-rhodamine n-butyl ester; Rhodamine 101 methyl ester; Rhodamine 123; Rhodamine 6G; Rhodamine 6G hexyl ester; tetrabromo-rhodamine 123; and tetramethyl-rhodamine ethyl ester.

Methylene Blue Dyes

Exemplary methylene blue derivatives include but are not limited to 1-methyl methylene blue; 1,9-dimethyl methylene blue; methylene blue; methylene blue (16 µM); methylene blue (14 µM); methylene violet; bromomethylene violet; 4-iodomethylene violet; 1,9-dimethyl-3-dimethyl-amino-7-diethyl-a-mino-phenothiazine; and 1,9-dimethyl-3-diethyl-amino-7-dibutyl-amino-phenot-hiazine.

Azo Dyes

Exemplary azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the one or more chromophores of the biophotonic materials disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine 0, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2, Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid, Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin Green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural green 3(chlorophyllin), Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red 0, Orange G, Orcein, Pararosanilin, Phloxine B, Picric acid, Ponceau 2R, Ponceau 6R, Ponceau B, Ponceau de Xylidine, Ponceau S, Primula, Purpurin, Pyronin B, phycobilins, Phycocyanins, Phycoerythrins. Phycoerythrincyanin (PEC), Phthalocyanines, Pyronin G, Pyronin Y, Quinine, Rhodamine B, Rosanilin, Rose Bengal, Saffron, Safranin 0, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue. Toluyline red, Tropaeolin G, Trypaflavine, Trypan blue, Uranin, Victoria blue 4R, Victoria blue B, Victoria green B, Vitamin B, Water blue I, Water soluble eosin, Xylidine ponceau, or Yellowish eosin.

In certain embodiments, the biophotonic material of the present disclosure includes any of the chromophores listed above, or a combination thereof, so as to provide a synergistic biophotonic effect at the application site.

Without being bound to any particular theory, a synergistic effect of the chromophore combinations means that the biophotonic effect is greater than the sum of their individual effects. Advantageously, this may translate to increased reactivity of the biophotonic material, faster or improved treatment time. Also, the treatment conditions need not be altered to achieve the same or better treatment results, such as time of exposure to light, power of light source used, and wavelength of light used. In other words, use of synergistic combinations of chromophores may allow the same or better treatment without necessitating a longer time of exposure to a light source, a higher power light source or a light source with different wavelengths.

In some embodiments, the material includes Eosin Y as a first chromophore and any one or more of Rose Bengal, Fluorescein, Erythrosine, Phloxine B, chlorophyllin as a second chromophore. It is believed that these combinations have a synergistic effect as they can transfer energy to one another when activated due in part to overlaps or close proximity of their absorption and emission spectra. This transferred energy is then emitted as fluorescence or leads to production of reactive oxygen species. This absorbed and reemitted light is thought to be transmitted throughout the composition, and also to be transmitted into the site of treatment.

In further embodiments, the material includes the following synergistic combinations: Eosin Y and Fluorescein; Fluorescein and Rose Bengal; Erythrosine in combination with Eosin Y, Rose Bengal or Fluorescein; Phloxine B in combination with one or more of Eosin Y, Rose Bengal, Fluorescein and Erythrosine. Other synergistic chromophore combinations are also possible.

By means of synergistic effects of the chromophore combinations in the material, chromophores which cannot normally be activated by an activating light (such as a blue light from an LED), can be activated through energy transfer from chromophores which are activated by the activating light. In this way, the different properties of photoactivated chromophores can be harnessed and tailored according to the cosmetic or the medical therapy required.

For example, Rose Bengal can generate a high yield of singlet oxygen when activated in the presence of molecular oxygen, however it has a low quantum yield in terms of emitted fluorescent light. Rose Bengal has a peak absorption around 540 nm and so can be activated by green light. Eosin Y has a high quantum yield and can be activated by blue light. By combining Rose Bengal with Eosin Y, one obtains a composition which can emit therapeutic fluorescent light and generate singlet oxygen when activated by blue light. In this case, the blue light photoactivates Eosin Y which transfers some of its energy to Rose Bengal as well as emitting some energy as fluorescence.

In some embodiments, the chromophore or chromophores are selected such that their emitted fluorescent light, on photoactivation, is within one or more of the green, yellow, orange, red and infrared portions of the electromagnetic spectrum, for example having a peak wavelength within the range of about 490 nm to about 800 nm. In certain embodiments, the emitted fluorescent light has a power density of between 0.005 to about 10 mW/cm$^2$, about 0.5 to about 5 mW/cm$^2$.

(b) Cohesive Matrix

The biophotonic materials of the present disclosure comprise a cohesive matrix made from one or more thickening agents, or a carrier medium. In other words, the biophotonic material of the present disclosure comprise one or more thickening agents, or a carrier medium which can form a cohesive matrix. These agents are present in an amount and ratio sufficient to provide a desired viscosity, flexibility, rigidity, tensile strength, tear strength, elasticity, and adhesiveness. The desired properties may be one of achieving a peelable film, or a rigid or flexible matrix. The thickening agents are selected so that the chromophore can remain photoactive in the cohesive matrix. The thickening agents are also selected according to the optical transparency of the cohesive matrix which they will form. The cohesive matrix should be able to transmit sufficient light to activate the at least one chromophore and, in embodiments where fluorescence is emitted by the activated chromophore, the cohesive matrix should also be able to transmit the emitted fluorescent light to tissues. It will be recognized by persons skilled in the art that the thickening agent is an appropriate medium for the chromophore selected. For example, the inventors have noted that some xanthene dyes do not fluoresce in non-hydrated media, so hydrated polymers or polar solvents may be used. The thickening agents should also be selected according to the intended use. For example, if the biophotonic material is to be applied onto tissue, the cohesive matrix is preferably a biocompatible material, or the cohesive matrix has an outside layer of a biocompatible material which will interface the tissue.

Thickening Agents

In some embodiments, the content of a thickening agent used to make the cohesive matrix is from about 0.001% to about 40% (w/w %) of the total weight. In certain embodiments, the total content of the thickening agent is about 0.001-0.01%, about 0.005-0.05%, about 0.01-0.1, about 0.05-0.5% about 0.1-1%, about 0.5-5%, about 1-5%, about 2.5-7.5%, about 5-10%, about 7.5-12.5%, about 10-15%, about 12.5-17.5%, or about 15-20%, or about 15-25%, or about 20-30%, or about 25-35%, or about 30-40%. It will be recognized by one of skill in the art that the viscosity, flexibility, rigidity, tensile strength, tear strength, elasticity, and adhesiveness can be adjusted by varying the content of the thickening material. Methods of determining viscosity, flexibility, rigidity, tensile strength, tear strength, elasticity, and adhesiveness are known in the art.

Thickening agents that can be used to prepare the biophotonic materials of the present disclosure include polymers, copolymers, and monomers of: vinylpyrrolidones, methacrylamides, acrylamides N-vinylimidazoles, carboxy vinyls, vinyl esters, vinyl ethers, silicones, polyethyleneoxides, polyethyleneglycols, vinylalcohols, sodium acrylates, acrylates, maleic acids, NN-d imethylacrylamides, diacetone acrylamides, acrylamides, acryloyl morpholine, pluronic, collagens, polyacrylamides, polyacrylates, polyvinyl alcohols, polyvinylenes, polyvinyl silicates, polyacrylates substituted with a sugar (e.g., sucrose, glucose, glucosamines, galactose, trehalose, mannose, or lactose), acylamidopropane sulfonic acids, tetramethoxyorthosilicates, methyltrimethoxyorthosilicates, tetraalkoxyorthosilicates, trialkoxyorthosilicates, glycols, propylene glycol, glycerine, polysaccharides, alginates, dextrans, cyclodextrin, celluloses, modified celluloses, oxidized celluloses, chitosans, chitins, guars, carrageenans, hyaluronic acids, inulin, starches, modified starches, agarose, methylcelluloses, plant gums, hylaronans, hydrogels, gelatins, glycosaminoglycans, carboxymethyl celluloses, hydroxycthyl celluloses, hydroxy propyl methyl celluloses, pectins, low-methoxy pectins, cross-linked dextrans, starch-acrylonitrile graft copolymers, starch sodium polyacrylate, hydroxyethyl methacrylates, hydroxyl ethyl acrylates, polyvinylene, polyethylvinylethers, polymethyl methacrylates, polystyrenes, polyurethanes, polyalkanoatcs, polylactic acids, polylactates, poly(3-hydroxybutyrate), sulfonated hydrogels, AMPS (2-acrylamido-2-methyl-1-propanesulfonic acid), SEM (sulfoethylmethacrylate), SPM (sulfopropyl methacrylate), SPA (sulfopropyl acrylate), N,N-dimethyl-N-methacryloxyethyl-N-(3-sulfopropyl)ammonium betaine, methacryllic acid amidopropyl-dimethyl ammonium sulfobetaine, SPI {itaconic acid-bis(1-propyl sulfonizacid-3) ester di-potassium salt}, itaconic acids, AMBC (3-acrylamido-3-methylbutanoic acid), beta-carboxyethyl acrylate (acrylic acid dimers), and maleic anhydride-methylvinyl ether polymers, derivatives thereof, salts thereof, acids thereof, combinations thereof, and the like.

Thickening agents also include poly (ethylene oxide) polymers (such as POLYOX from Dow Chemical), linear PVP and cross-linked PVP, PEG/PPG copolymers (such as BASF Pluracare L1220), ethylene oxide (E0)—propylene oxide (PO) block copolymers (such as polymers sold under the trade mark Pluronic available from BASF Corporation), ester gum, shellac, pressure sensitive silicone adhesives (such as BioPSA from Dow-Corning), or mixtures thereof. In some embodiments, a copolymer comprises (PVM/MA). In an embodiment, a copolymer comprises poly (methylvinylether/maleic anhydride). In some embodiments, a copolymer comprises poly (methylvinylether/maleic acid). In some embodiments, a copolymer comprises poly (methylvinylether/maleic acid) half esters. In some embodiments, a copolymer comprises poly (methylvinylether/maleic acid) mixed salts.

Thickening agents can also include carbomers which are a synthetic high molecular weight polymer of acrylic acid that is crosslinked with either allylsucrose or allylethers of pentaerythritol having a molecular weight of about $3 \times 10^6$. The gelation mechanism depends on neutralization of the carboxylic acid moiety to form a soluble salt. The polymer is hydrophilic and produces sparkling clear gels when neutralized. Carbomers are available as fine white powders which disperse in water to form acidic colloidal suspensions (a 1% dispersion has approx. pH 3) of low viscosity. Neutralization of these suspensions using a base, for example sodium, potassium or ammonium hydroxides, low molecular weight amines and alkanolamines, results in the formation of clear translucent gels.

In one embodiment of the disclosure, the carbomer is Carbopol®. Such polymers are commercially available from B.F. Goodrich or Lubrizol under the designation Carbopol® 71G NF, 420, 430, 475, 488, 493, 910, 934, 934P, 940, 971PNF, 974P NF, 980 NF, 981 NF and the like. Carbopols are versatile controlled-release polymers, as described by Brock (Pharmacotherapy, 14:430-7 (1994)) and Durrani (Pharmaceutical Res. (Supp.) 8:S-135 (1991)), and belong to a family of carbomers which are synthetic, high molecular weight, non-linear polymers of acrylic acid, cross-linked with polyalkenyl polyether. In some embodiments, the carbomer is Carbopol® 974P NF, 980 NF, 5984 EP, ETD 2020NF, Ultrez 10 NF, 934 NF, 934P NF or 940 NF. In certain embodiments, the carbomer is Carbopol® 980 NF, ETD 2020 NF, Ultrez 10 NF, Ultrez 21 or 1382 Polymer, 1342 NF, 940 NF.

In certain embodiments of the disclosure, the thickening agent or the carrier medium may comprise gelatin. For example, the cohesive matrix may comprise at least about 5%, about 5 to about 25 weight %, or about 10 to about 20 weight % gelatin within the cohesive biophotonic material. Alternatively, a lower weight percentage of gelatin may be used together with chemical cross-linkers or any other cross-linking means.

In certain embodiments of the disclosure, the thickening agent or the carrier medium may comprise sodium hyaluronate, which may be present in an amount of about 2% to 10 about 14%.

The biophotonic material of the present disclosure may be water soluble. Alternatively, the biophotonic material of the present disclosure may optionally include a water-insoluble or liposoluble substrate. By "water insoluble", it is meant that the substrate does not dissolve in or readily break apart upon immersion in water. In some embodiments, the water-insoluble substrate is the implement or vehicle for delivering the treatment composition to the skin or target tissue. A wide variety of materials can be used as the water-insoluble substrate. The following non-limiting characteristics may be desirable: (i) sufficient wet strength for use, (ii) sufficient softness, (iii) sufficient thickness, (iv) appropriate size, (v) air permeability, and (vi) hydrophilicity.

Non-limiting examples of suitable water-insoluble substrates which meet the above criteria include nonwoven substrates, woven substrates, hydroentangled substrates, air entangled substrates, natural sponges, synthetic sponges, polymeric netted meshes, and the like. Preferred embodiments employ nonwoven substrates since they are economical and readily available in a variety of materials. By "nonwoven", it is meant that the layer is comprised of fibers which are not woven into a fabric but rather are formed into a sheet, mat, or pad layer.

In one embodiment of the disclosure, the thickening agent or the cohesive agent may comprise a silicone membrane. In this embodiment, the chromophore or chromophores can be included directly within the silicone membrane or if they are water soluble within inclusions in the membrane as an aqueous phase. For example, the aqueous phase may be present as a micro-emulsion within the silicone. The aqueous phase may be a liquid or a semi-solid. The aqueous phase may further comprise a stabilizing agent to stabilize the emulsion such as gelatin or CMC. The aqueous phase may comprise up to 40 wt % of the silicone polymer phase.

Antimicrobials

Antimicrobials kill microbes or inhibit their growth or accumulation, and are optionally included in the biophotonic materials of the present disclosure. Exemplary antimicrobials (or antimicrobial agent) are recited in U.S. Patent Application Publications 20040009227 and 20110081530. Suitable antimicrobials for use in the methods and compositions of the present disclosure include, but not limited to, hydrogen peroxide, urea hydrogen peroxide, benzoyl peroxide, phenolic and chlorinated phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Hydrogen peroxide ($H_2O_2$) is a powerful oxidizing agent, and breaks down into water and oxygen and does not form any persistent, toxic residual compound. A suitable range of concentration over which hydrogen peroxide can be used in the biophotonic material is from about 0.1% to about 3%, about 0.1 to 1.5%, about 0.1% to about 1%, about 1%, less than about 1%.

Urea hydrogen peroxide (also known as urea peroxide, carbamide peroxide or percarbamide) is soluble in water and contains approximately 35% hydrogen peroxide. A suitable range of concentration over which urea peroxide can be used in the biophotonic material of the present disclosure is less than about 0.25%, or less than about 0.3%, from 0.001 to 0.25%, or from about 0.3% to about 5%. Urea peroxide breaks down to urea and hydrogen peroxide in a slow-release fashion that can be accelerated with heat or photochemical reactions.

Benzoyl peroxide consists of two benzoyl groups (benzoic acid with the H of the carboxylic acid removed) joined by a peroxide group. It is found in treatments for acne, in concentrations varying from 2.5% to 10%. The released peroxide groups are effective at killing bacteria. Benzoyl peroxide also promotes skin turnover and clearing of pores, which further contributes to decreasing bacterial counts and reduce acne. Benzoyl peroxide breaks down to benzoic acid and oxygen upon contact with skin, neither of which is toxic. A suitable range of concentration over which benzoyl peroxide can be used in the matrix biophotonic is from about 2.5% to about 5%.

According to certain embodiments, the biophotonic material of the present disclosure may optionally comprise one or more additional components, such as oxygen-rich compounds as a source of oxygen radicals. Peroxide compounds are oxidants that contain the peroxy group (R—O—O—R), which is a chainlike structure containing two oxygen atoms, each of which is bonded to the other and a radical or some element. When a biophotonic material of the present disclosure comprising an oxidant is illuminated with light, the chromophores are excited to a higher energy state. When the chromophores' electrons return to a lower energy state, they emit photons with a lower energy level, thus causing the emission of light of a longer wavelength (Stokes' shift). In the proper environment, some of this energy is transferred to oxygen or the reactive hydrogen peroxide and causes the formation of oxygen radicals, such as singlet oxygen. The singlet oxygen and other reactive oxygen species generated by the activation of the biophotonic material are thought to operate in a hormetic fashion. That is, a health beneficial effect that is brought about by the low exposure to a normally toxic stimuli (e.g. reactive oxygen), by stimulating and modulating stress response pathways in cells of the targeted tissues. Endogenous response to exogenous generated free radicals (reactive oxygen species) is modulated in increased defense capacity against the exogenous free radicals and induces acceleration of healing and regenerative processes. Furthermore, activation of the oxidant may also produce an antibacterial effect. The extreme sensitivity of bacteria to exposure to free radicals makes the biophotonic material of the present disclosure potentially a bactericidal composition.

Specific phenolic and chlorinated phenolic antimicrobial agents that can be used in the disclosure include, but are not limited to: phenol; 2-methyl phenol; 3-methyl phenol; 4-methyl phenol; 4-ethyl phenol; 2,4-dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n-hexyl phenol; 4-n-heptyl phenol; mono- and poly-alkyl and aromatic halophenols; p-chlorophenyl; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p-chlorophenol; cyclohexyl p-chlorophenol; n-heptyl p-chlorophenol; n-octyl; p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-m-methyl p-chlorophenol; o-benzyl-m, m-dimethyl p-chlorophenol; o-phenylethyl p-chlorophenol; o-phenylethyl-m-methyl p-chlorophenol; 3-methyl p-chlorophenol 3,5-dimethyl p-chlorophenol, 6-ethyl-3-methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2-ethyl-3-methyl p-chlorophenol; 2-sec-amyl-3,5-dimethyl p-chlorophenol; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; ten-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol; 2,4-dichloro-3,5-dimethylphenol; 3,4,5,6-tetabrorno-2-methylphenol-; 5-methyl-2-pentylphenol; 4-isopropyl-3-methylphenol; para-chloro-metaxylenol (PCMX); chlorothymol; phenoxyethanol; phenoxyisopropanol; and 5-chloro-2-hydroxydiphenylmethane.

Resorcinol and its derivatives can also be used as antimicrobial agents. Specific resorcinol derivatives include, but are not limited to: methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2,4-dihydroxydiphenyl methane; 4-chloro-2,4-dihydroxydiphenyl methane; 5-bromo-2,4-dihydroxydiphenyl methane; and 4'-bromo-2,4-dihydroxydiphenyl methane.

Specific bisphenolic antimicrobial agents that can be used in the disclosure include, but are not limited to: 2,2'-methylene bis-(4-chlorophenol); 2,4,4'trichloro-2'-hydroxydiphenyl ether, which is sold by Ciba Geigy, Florham Park, N.J. under the tradename Triclosan®; 2,2'-methylene bis-(3,4,6-trichlorophenol); 2,2-methylene bis-(4-chloro-6-bromophenol); bis-(2-hydroxy-3,5-dichlorop-henyl) sulphide; and bis-(2-hydroxy-5-chlorobenzyl)sulphide.

Specific benzoic esters (parabens) that can be used in the disclosure include, but are not limited to: methylparaben; propylparaben; butylparaben; ethylparaben; isopropylparaben; isobutylparaben; benzylparaben; sodium methylparaben; and sodium propylparaben.

Specific halogenated carbanilides that can be used in the disclosure include, but are not limited to: 3,4,4'-trichlorocarbanilides, such as 3-(4-chlorophenyl)-1-(3,4-dichlorphenyl)urea sold under the tradename Triclocarban® by Ciba-Geigy, Florham Park, N.J.; 3-trifluoromethyl-4,4'-dichlorocarbanilide; and 3,3',4-trichlorocarbanilide.

Specific polymeric antimicrobial agents that can be used in the disclosure include, but are not limited to: polyhexamethylene biguanide hydrochloride; and poly(iminoimidocarbonyl iminoimidocarbonyl inohexamethylene hydrochloride), which is sold under the tradename Vantocil® IB.

Specific thazolines that can be used in the disclosure include, but are not limited to that sold under the tradename Micro-Check®; and 2-n-octyl-4-isothiazolin-3-one, which is sold under the tradename Vinyzene®1T-3000 DIDP.

Specific trichloromethylthioimides that can be used in the disclosure include, but are not limited to: N-(trichloromethylthio) phthalimide, which is sold under the tradename Fungitrol®; and N-trichloromethylthio-4-cyclohexene-1,2-dicarboximide, which is sold under the tradename Vancide®.

Specific natural antimicrobial agents that can be used in the disclosure include, but are not limited to, oils of: anise; lemon; orange; rosemary; wintergreen; thyme; lavender; cloves; hops; tea tree; citronella; wheat; barley; lemongrass; cedar leaf; cedarwood; cinnamon; fleagrass; geranium; sandalwood; violet; cranberry; eucalyptus; vervain; peppermint; gum benzoin; basil; fennel; fir; balsam; menthol; ocmea origanuin; hydastis; carradensis; Berberidaceac daceae; Ratanhiae longa; and Curcuma longa. Also included in this class of natural antimicrobial agents are the key chemical components of the plant oils which have been found to provide antimicrobial benefit. These chemicals include, but are not limited to: anethol; catechole; camphene; thymol; eugenol; eucalyptol; ferulic acid; farnesol; hinokitiol; tropolone; limonene; menthol; methyl salicylate; carvacol; terpineol; verbenone; berberine; ratanhiae extract; caryophellene oxide; citronellic acid; curcumin; nerolidol; and geraniol.

Specific metal salts that can be used in the disclosure include, but are not limited to, salts of metals in groups 3a-5a, 3b-7b, and 8 of the periodic table. Specific examples of metal salts include, but are not limited to, salts of: aluminum; zirconium; zinc; silver; gold; copper; lanthanum; tin; mercury; bismuth; selenium; strontium; scandium; yttrium; cerium; praseodymiun; neodymium; promethum; samarium; europium; gadolinium; terbium; dysprosium; holmium; erbium; thalium; ytterbium; lutetium; and mixtures thereof. An example of the metal-ion based antimicrobial agent is sold under the tradename HealthShield®, and is manufactured by HealthShield Technology, Wakefield, Mass.

Specific broad-spectrum antimicrobial agents that can be used in the disclosure include, but are not limited to, those that are recited in other categories of antimicrobial agents herein.

Additional antimicrobial agents that can be used in the methods of the disclosure include, but are not limited to: pyrithiones, and in particular pyrithione-including zinc complexes such as that sold under the tradename Octopirox®; dimethyidimethylol hydantoin, which is sold under the tradename Glydant®; methylchloroisothiazolinone/methylisothiazolinone, which is sold under the tradename Kathon CG®; sodium sulfite; sodium bisulfite; imidazolidinyl urea, which is sold under the tradename Germall 115®; diazolidinyl urea, which is sold under the tradename Germall 11®; benzyl alcohol v2-bromo-2-nitropropane-1,3-diol, which is sold under the tradename Bronopol®; formalin or formaldehyde; iodopropenyl butylcarbamate, which is sold under the tradename Polyphase P100®; chloroacetamide; methanamine; methyldibromonitrile glutaronitrile (1,2-dibromo-2,4-dicyanobutane), which is sold under the tradename Tektamer®; glutaraldehyde; 5-bromo-5-nitro-1,3-dioxane, which is sold under the tradename Bronidox®; phenethyl alcohol; o-phenylphenol/sodium o-phenylphenol sodium hydroxymethylglycinate, which is sold under the tradename Suttocide A®; polymethoxy bicyclic oxazolidine; which is sold under the tradename Nuosept C®; dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether, which is sold under the tradename Triclosan® and is available from Ciba-Geigy, Florham Park, N.J.; and 2,2'-dihydroxy-5,5'-dibromo-diphenyl ether.

Additional antimicrobial agents that can be used in the methods of the disclosure include those disclosed by U.S. Pat. Nos. 3,141,321; 4,402,959; 4,430,381; 4,533,435; 4,625,026; 4,736,467; 4,855,139; 5,069,907; 5,091.102; 5,639,464; 5,853,883; 5,854,147; 5,894,042; and 5,919,554, and U.S. Pat. Appl. Publ. Nos. 20040009227 and 20110081530.

(4) Optical Properties of the Biophotonic Materials

In certain embodiments, biophotonic materials of the present disclosure are substantially transparent or translucent. The % transmittance of the biophotonic material can be measured in the range of wavelengths from 250 nm to 800 nm using, for example, a Perkin-Elmer Lambda 9500 series UV-visible spectrophotometer. In some embodiments, transmittance within the visible range is measured and averaged. In some other embodiments, transmittance of the biophotonic material is measured with the chromophore omitted. As transmittance is dependent upon thickness, the thickness of each sample can be measured with calipers prior to loading in the spectrophotometer. Transmittance values can be normalized according to $$F_{T-corr}(\lambda, t_2) = [e^{-\sigma_t(\lambda)t_1}]^{\frac{t_2}{t_1}} = [F_{T-corr}(\lambda, t_1)]^{\frac{t_2}{t_1}},$$

where $t_1$=actual specimen thickness, $t_2$=thickness to which transmittance measurements can be normalized. In the art, transmittance measurements are usually normalized to 1 cm.

In certain embodiments, the biophotonic materials are substantially opaque. In these embodiments, the biophotonic materials may include light transmitting structures such as fibres, particles, networks, which are made of materials which can transmit light. The light transmitting structures can be waveguides such as optical fibres.

In some embodiments, the biophotonic material has a transmittance that is more than about 20%, 30%, 40%, 50%, 60%, 70%, or 75% within the visible range. In some embodiments, the transmittance exceeds 40%, 41%, 42%, 43%, 44%, or 45% within the visible range.

(5) Forms of the Biophotonic Materials

The biophotonic materials of the present disclosure may be in the form of a cohesive film or matrix containing at least one chromophore. The cohesive film or matrix may be a cohesive gel, or a paste, a putty, a semi-solid, or a solid.

The biophotonic materials of the present disclosure may be deformable. They may be elastic or non-elastic (i.e. flexible or rigid). The biophotonic materials, for example, may be in a peel-off form ('peelable') to provide ease and speed of use. In certain embodiments, the tear strength and/or tensile strength of the peel-off form is greater than its adhesion strength. This may help handleability of the material. It will be recognized by one of skill in the art that the properties of the peel-off biophotonic material such as cohesiveness, flexibility, elasticity, tensile strength, and tearing strength, can be determined and/or adjusted by methods known in the art such as by selecting suitable thickening agents and adapting their relative ratios.

The biophotonic material may be in a pre-formed shape. In certain embodiments, the pre-formed shape is in the form of, including, but not limited to, a film, a face mask, a patch, a dressing, or bandage. In certain embodiments, the pre-formed shapes can be customized for the individual user by trimming to size. In certain embodiments, perforations are provided around the perimeter of the pre-formed shape to facilitate trimming. In certain embodiments, the pre-shaping can be performed manually or by mechanical means such as 3-D printing. In the case of the 3-D printing the size of the area to be treated can be imaged, such as a wound or a face, then a 3-D printer configured to build or form a cohesive biophotonic material to match the size and shape of the imaged treatment area.

A biophotonic material of the disclosure can be configured with a shape and/or size for application to a desired portion of a subject's body. For example, the biophotonic material can be shaped and sized to correspond with a desired portion of the body to receive the biophotonic treatment. Such a desired portion of skin can be selected from, but not limited to, the group consisting of a skin, head, forehead, scalp, nose, cheeks, lips, ears, face, neck, shoulder, arm pit, arm, elbow, hand, finger, abdomen, chest, stomach, back, buttocks, sacrum, genitals, legs, knee, feet, toes, nails, hair, any boney prominences, and combinations thereof, and the like. Thus, the biophotonic material of the disclosure can be shaped and sized to be applied to any portion of skin on a subject's body. For example, the biophotonic material can be sock, hat, glove or mitten shaped. In embodiments where the biophotonic material is elastic or rigid, it can be peeled-off without leaving any residue on the tissue.

In certain embodiments, the biophotonic material is in the form of an elastic and peelable face mask, which may be pre-formed. In other embodiments, the biophotonic material is in the form of a non-elastic (rigid) face mask, which may also be pre-formed. The mask can have openings for one or more of the eyes, nose and mouth. In a further embodiment, the openings are protected with a covering, or the exposed skin such as on the nose, lips or eyes are protected using for example cocoa butter. In certain embodiments, the pre-formed face mask is provided in the form of multiple parts, e.g., an upper face part and a lower face part. In certain embodiments, the uneven proximity of the face to a light source is compensated for, e.g., by adjusting the thickness of the mask, or by adjusting the amount of chromophore in the different areas of the mask, or by blocking the skin in closest proximity to the light. In certain embodiments, the pre-formed shapes come in a one-size fits all form.

In certain aspects, the mask (or patch) is not pre-formed and is applied e.g., by spreading a composition making up the mask (or patch), on the skin or target tissue, or alternatively by spraying, smearing, dabbing or rolling the composition on target tissue. It can then be converted to a peel-off form after application, by means such as, but not limited to, drying, illumination with light, change in temperature or pH upon application to the skin or tissue. The mask (or patch) can then be peeled off without leaving any flakes on the skin or tissue, preferably without wiping or washing.

In certain aspects, the biophotonic material may have shape memory properties. For example, the biophotonic material can include a shape memory material, such as a shape memory polymer whose original shape is reverted to on activation by light. The original shape can be a flat or concave configuration which allows the film/matrix to be readily peeled off the tissue. The shape memory material may be included as a layer attached to the biophotonic material, or integrated with the biophotonic material.

In certain aspects, the biophotonic material forms part of a composite and can include fibres, particulates, non-biophotonic layers or biophotonic layers with the same or different compositions.

In certain embodiments, the biophotonic material may comprise a plurality of waveguides extending at least partially through the biophotonic material or contained at least partially within the biophotonic material. The waveguides can be attached to a light source to thereby illuminate the biophotonic material from within. The biophotonic material may further include the light source attached to the waveguides. The waveguides can be optical fibres which can transmit light, not only from their ends, but also from their body. For example, made of polycarbonate or polymethylmethacrylate or any other suitable material.

In a different embodiment, the biophotonic material comprises a layer of a woven or non-woven fabric dressing or a mask. Waveguides or a light source may be included within the dressing or mask fabric. For example, the dressing or mask fabric can be in the form of an envelope which receives the biophotonic material, and which comprises at least one light emitting surface.

In certain aspects, the biophotonic material is formed as a filter. For example, the biophotonic material can be made to have a shape arid a size which can be connected to, or spaced from, a light emitting surface of a lamp. In one embodiment, the lamp can be a hand-held lamp such as a torch or a dentist's curing lamp. The lamp with the biophotonic filter can then be used to treat tissue sites of patient in a contacting or non-contacting manner. In this embodiment, the filter has a body having a first end which is sized and shaped to be connectable to a light emitting surface, and a second end shaped to treat tissues.

In certain aspects, the biophotonic material is formed as a waveguide. In certain embodiments, at least one chromophore is included in an elongate solid matrix having good light propagation properties and appropriate mechanical properties. The waveguide may be flexible. The waveguide can be shaped as an optical fibre. Such an optical fibre can be connected to a light source, and the at least one chromophore in the cohesive matrix activated by the light source to deliver therapeutic fluorescent light to hard to reach places, such as internal cavities and periodontal pockets. Polymethylmethacrylate is an example of an appropriate cohesive matrix for use as a biophotonic waveguide. Such a waveguide may additionally include a coating to prevent light dissipation from along its length.

In other aspects, the biophotonic material comprising at least one chromophore and a cohesive matrix is in the form of particulates. Material processing techniques known in the art can be used to form particulates of any shape or size. These particulates can be contained in semi-solid or liquid preparations. For example, such biophotonic particulates can be used in skin preparations such as creams, emulsions to provide therapeutic effect to the skin. In this case, a biocompatible solid matrix is used and can be used to encapsulate all types of chromophores, even those not well tolerated by the skin.

The biophotonic materials of the present disclosure may have a thickness of from about 0.1 mm to about 50 mm, about 0.5 mm to about 20 mm, or about 1 mm to about 10 mm. It will be appreciated that the thickness of the biophotonic materials will vary based on the intended use. In some embodiments, the biophotonic material has a thickness of from about 0.1-1 mm. In some embodiments, the biophotonic material has a thickness of about 0.5-1.5 mm, about 1-2 mm, about 1.5-2.5 mm, about 2-3 mm, about 2.5-3.5 mm, about 3-4 mm, about 3.5-4.5 mm, about 4-5 mm, about 4.5-5.5 mm, about 5-6 mm, about 5.5-6.5 mm, about 6-7 mm, about 6.5-7.5 mm, about 7-8 mm, about 7.5-8.5 mm, about 8-9 mm, about 8.5-9.5, about 9-10 mm, about 10-11 mm, about 11-12 mm, about 12-13 mm, about 13-14 mm, about 14-15 mm, about 15-16 mm, about 16-17 mm, about 17-18 mm, about 18-19 mm, about 19-20 mm, about 20-22 mm, about 22-24 mm, about 24-26 mm, about 26-28 inm, about 28-30 mm, about 30-35 mm, about 35-40 mm, about 40-45 mm, about 45-50 mm.

The tensile strength of the biophotonic materials will vary based on the intended use. The tensile strength can be determined by performing a tensile test and recording the force and displacement. These are then converted to stress (using cross sectional area) and strain; the highest point of the stress-strain curve is the "ultimate tensile strength." In some embodiments, tensile strength can be characterized using a 500N capacity tabletop mechanical testing system (#5942R4910, Instron®) with a 5N maximum static load cell (#102608, Instron). Pneumatic side action grips can be used to secure the samples (#2712-019, Instron). In some embodiments, a constant extension rate (for example, of about 2 mm/min) until failure can be applied and the tensile strength is calculated from the stress vs. strain data plots. In some embodiments, the tensile strength can be measured using methods as described in or equivalent to those described in American Society for Testing and Materials tensile testing methods such as ASTM D638, ASTM D882 and ASTM D412.

In some embodiments, the biophotonic material has a tensile strength of from about 1-50 kPa, 1 to about 1000 kPa, 1 to about 500 kPa, 50 kPa to about 600 kPa. In some embodiments, the tensile strength is from about 75 kPa to about 500 kPa, from about 100 kPa to about 200 kPa, 100-300 kPa, 400 kPa, from about 150 kPa to about 350 kPa, or from about 200 kPa to about 300 kPa.

In some embodiments, the tensile strength is at least about 50 kPa, at least about 75 kPa, at least about 100 kPa, at least about 150 kPa, at least about 200 kPa, at least about 250 kPa, at least about 300 kPa, at least about 350 kPa, at least about 400 kPa, at least about 450 kPa, at least about 500 kPa, at least about 550 kPa or at least about 600 kPa.

In some embodiments, the tensile strength of the biophotonic material is up to about 8 MPa.

The tear strength of the biophotonic material will vary depending on the intended use. The tear strength property of the biophotonic material can be tested using a 500N capacity tabletop mechanical testing system (#5942R4910, Instron) with a 5N maximum static load cell (#102608, Instron). Pneumatic side action grips can be used to secure the samples (#2712-019, Instron). Samples can be tested with a constant extension rate (for example, of about 2 mm/min) until failure. In accordance with the invention, tear strength is calculated as the force at failure divided by the average thickness (N/mm).

In some embodiments, the biophotonic material has a tear strength of from about 0.1 N/mm to about 1 N/mm. In some embodiments, the tear strength is from about 0.20 N/mm to about 0.40 N/mm, from about 0.25 N/mm to about 0.35 N/mm, from about 0.25 N/mm to about 0.45 N/mm, from about 0.35 N/mm to about 0.535 N/mm, from about 0.45 N/mm to about 0.65 N/mm, from about 0.55 N/mm to about 0.75 N/mm, from about 0.65 Nimm to about 0.85 N/mm, from about 0.75 N/mm to about 0.95 N/mm.

In some embodiments, the tear strength is at least about 0.10 N/mm, at least about 0.15 N/mm, at least about 0.20 N/mm, at least about 0.25 Winin, at least about 0.30 N/mm, at least about 0.35 N/mm, at least about 0.40 N/mm, at least about 0.45 N/mm, at least about 0.55 N/mm or at least about 1 N/mm.

The adhesion strength of the biophotonic material will vary depending on the intended use. Adhesion strength can be determined in accordance with ASTM D-3330-78, PSTC-101 and is a measure of the force required to remove a biophotonic material from a test panel at a specific angle and rate of removal. In some embodiments, a predetermined size of a biophotonic material is applied to a horizontal surface of a clean glass test plate. A hard rubber roller is used to firmly apply the piece and remove all discontinuities and entrapped air. The free end of the piece of biophotonic material is then doubled back nearly touching itself so that the angle of removal of the piece from the glass plate will be 180 degrees. The free end of the piece of biophotonic material is attached to the adhesion tester scale (e.g. an Instron tensile tester or Harvey tensile tester). The test plate is then clamped in the jaws of the tensile testing machine capable of moving the plate away from the scale at a predetermined constant rate. The scale reading in kg is recorded as the biophotonic material is peeled from the glass surface.

In some embodiments, the adhesion strength can be measured by taking into account the static friction of the biophotonic material. For some embodiments of the cohesive biophotonic materials of the present disclosure, the adhesive properties are linked to their levels of static friction, or stiction. In these cases, the adhesion strength can be measured by placing the sample on a test surface and pulling one end of the sample at an angle of approximately 0° (substantially parallel to the surface) whilst applying a known downward force (e.g. a weight) on the sample and measuring the weight at which the sample slips from the surface. The normal force $F_n$, is the force exerted by each surface on the other in a perpendicular (normal) direction to the surface and is calculated by multiplying the combined weight of the sample and the weight by the gravity constant (g) ($9.8$ m/s$^2$). The biophotonic material with the weight on top is then pulled away from a balance until the biophotonic material slips from the surface and the weight is recorded on the scale. The weight recorded on the scale is equivalent to the force required to overcome the friction. The force of friction (Fr) is then calculated by multiplying the weight recorded on the scale by g. Since $F_f \leq \mu f_n$, (Coulomb's friction law), the friction coefficient $\mu$ can be obtained by dividing $F_f/F_n$. The stress required to shear a material from a surface (adhesion strength) can then be calculated from the friction coefficient, $\mu$, by multiplying the weight of the material by the friction coefficient.

In some embodiments, the biophotonic material has an adhesion strength that is less than its tensile strength. In some embodiments, the biophotonic material has an adhesion strength that is less than its tear strength.

In some embodiments, the biophotonic material has an adhesion strength of from about 0.01 N/mm to about 0.60 N/mm. In some embodiments, the adhesion strength is from about 0.20 N/mm to about 0.40 N/mm, or from about 0.25 N/mm to about 0.35 N/mm. In some embodiments, the adhesion strength is less than about 0.10 N/mm, less than about 0.15 N/mm, less than about 0.20 N/mm, less than about 0.25 N/mm, less than about 0.30 N/mm, less than about 0.35 N/mm, less than about 0.40 N/mm, less than about 0.45 N/mm, less than about 0.55 N/mm or less than about 0.60 N/mm.

(6) Methods of Use

The biophotonic materials of the present disclosure may have cosmetic and/or medical benefits. They can be used to promote skin rejuvenation and skin conditioning, promote the treatment of a skin disorder such as acne, eczema or psoriasis, promote tissue repair, and promote wound healing including periodontitis pockets. They can be used to treat acute inflammation. Acute inflammation can present itself as pain, heat, redness, swelling and loss of function. It includes those seen in allergic reactions such as insect bites e.g.; mosquito, bees, wasps, poison ivy, or post-ablative treatment.

Accordingly, in certain embodiments, the present disclosure provides a method for treating acute inflammation.

In certain embodiments, the present disclosure provides a method for providing skin rejuvenation or for improving skin condition, treating a skin disorder, preventing or treating scarring, and/or accelerating wound healing and/or tissue repair, the method comprising: applying a biophotonic material of the present disclosure to the area of the skin or tissue in need of treatment, and illuminating the biophotonic material with light having a wavelength that overlaps with an absorption spectrum of the chromophore(s) present in the biophotonic material.

In the methods of the present disclosure, any source of actinic light can be used. Any type of halogen, LED or plasma arc lamp, or laser may be suitable. The primary characteristic of suitable sources of actinic light will be that they emit light in a wavelength (or wavelengths) appropriate for activating the one or more photoactivators present in the composition. In one embodiment, an argon laser is used. In another embodiment, a potassium-titanyl phosphate (KTP) laser (e.g. a GreenLight™ laser) is used. In yet another embodiment, a LED lamp such as a photocuring device is the source of the actinic light. In yet another embodiment, the source of the actinic light is a source of light having a wavelength between about 200 to 800 nm. In another embodiment, the source of the actinic light is a source of visible light having a wavelength between about 400 and 600 nm. In another embodiment, the source of the actinic light is a source of visible light having a wavelength between about 400 and 700 nm. In yet another embodiment, the source of the actinic light is blue light. In yet another embodiment, the source of the actinic light is red light. In yet another embodiment, the source of the actinic light is green light. Furthermore, the source of actinic light should have a suitable power density. Suitable power density for non-collimated light sources (LED, halogen or plasma lamps) are in the range from about 0.1 mW/cm$^2$ to about 200 mW/cm$^2$.

Suitable power density for laser light sources are in the range from about 0.5 mW/cm$^2$ to about 0.8 mW/cm$^2$.

In some embodiments of the methods of the present disclosure, the light has an energy at the subject's skin surface of between about 0.1 mW/cm$^2$ and about 500 mW/cm$^2$, or 0.1-300 mW/cm$^2$, or 0.1-200 mW/cm$^2$, wherein the energy applied depends at least on the condition being treated, the wavelength of the light, the distance of the skin from the light source and the thickness of the biophotonic material. In certain embodiments, the light at the subject's skin is between about 1-40 mW/cm$^2$, or 20-60 mW/cm$^2$, or 40-80 mW/cm$^2$, or 60-100 mW/cm$^2$, or 80-120 mW/cm$^2$, or 100-140 mW/cm$^2$, or 30-180 mW/cm$^2$, or 120-160 mW/cm$^2$, or 140-180 mW/cm$^2$, or 160-200 mW/cm$^2$, or 110-240 mW/cm$^2$, or 110-150 mW/cm$^2$, or 190-240 mW/cm$^2$.

The activation of the chromophore(s) within the biophotonic material may take place almost immediately on illumination (femto- or pico seconds). A prolonged exposure period may be beneficial to exploit the synergistic effects of the absorbed, reflected and reemitted light of the biophotonic material of the present disclosure and its interaction with the tissue being treated. In one embodiment, the time of exposure to actinic light of the tissue or skin or biophotonic material is a period between 1 minute and 5 minutes. In another embodiment, the time of exposure to actinic light of the tissue or skin or biophotonic material is a period between 1 minute and 5 minutes. In some other embodiments, the biophotonic material is illuminated for a period between 1 minute and 3 minutes. In certain embodiments, light is applied for a period of 1-30 seconds, 15-45 seconds, 30-60 seconds, 0.75-1.5 minutes, 1-2 minutes, 1.5-2.5 minutes, 2-3 minutes, 2.5-3.5 minutes, 3-4 minutes, 3.5-4.5 minutes, 4-5 minutes, 5-10 minutes, 10-15 minutes, 15-20 minutes, or 20-30 minutes. The treatment time may range up to about 90 minutes, about 80 minutes, about 70 minutes, about 60 minutes, about 50 minutes, about 40 minutes or about 30 minutes. It will be appreciated that the treatment time can be adjusted in order to maintain a dosage by adjusting the rate of fluence delivered to a treatment area. For example, the delivered fluence may be about 4 to about 60 J/cm$^2$, about 10 to about 60 J/cm$^2$, about 10 to about 50 J/cm$^2$, about 10 to about 40 J/cm$^2$, about 10 to about 30 J/cm$^2$, about 20 to about 40 J/cm$^2$, about 15 J/cm$^2$ to 25 J/cm$^2$, or about 10 to about 20 J/cm$^2$.

In certain embodiments, the biophotonic material may be re-illuminated at certain intervals. In yet another embodiment, the source of actinic light is in continuous motion over the treated area for the appropriate time of exposure. In yet another embodiment, the biophotonic composition may be illuminated until the biophotonic composition is at least partially photobleached or fully photobleached.

In certain embodiments, the chromophore(s) in the cohesive matrix can be photoexcited by ambient light including from the sun and overhead lighting. In certain embodiments, the chromophore(s) can be photoactivated by light in the visible range of the electromagnetic spectrum. The light can be emitted by any light source such as sunlight, light bulb, an LED device, electronic display screens such as on a television, computer, telephone, mobile device, flashlights on mobile devices. In the methods of the present disclosure, any source of light can be used. For example, a combination of ambient light and direct sunlight or direct artificial light may be used. Ambient light can include overhead lighting such as LED bulbs, fluorescent bulbs etc, and indirect sunlight.

In the methods of the present disclosure, the biophotonic material may be removed from the skin following application of light. In some embodiments the biophotonic material is peeled off from the skin following application of light. In some embodiments, the biophotonic material is removed as a single piece from the skin following application of light. In other embodiments, the biophotonic material is left on the tissue for an extended period of time and re-activated with direct or ambient light at appropriate times to treat the condition.

In certain embodiments of the method of the present disclosure, the biophotonic material can be applied to the tissue, such as on the face, once, twice, three times, four times, five times or six times a week, daily, or at any other frequency. The total treatment time can be one week, two weeks, three weeks, four weeks, five weeks, six weeks, seven weeks, eight weeks, nine weeks, ten weeks, eleven weeks, twelve weeks, or any other length of time deemed appropriate. In certain embodiments, the total tissue area to be treated may be split into separate areas (cheeks, forehead), and each area treated separately. For example, the composition may be applied topically to a first portion, and that portion illuminated with light, and the biophotonic composition then removed. Then the composition is applied to a second portion, illuminated and removed. Finally, the composition is applied to a third portion, illuminated and removed.

In certain embodiments, the biophotonic material can be used following wound closure to optimize scar revision. In this case, the biophotonic material may be applied at regular intervals such as once a week, or at an interval deemed appropriate by the physician.

In certain embodiments, the biophotonic material can be used following acne treatment to maintain the condition of the treated skin. In this case, the biophotonic material may be applied at regular intervals such as once a week, or at an interval deemed appropriate by the physician.

In certain embodiments, the biophotonic material can be used following ablative skin rejuvenation treatment to maintain the condition of the treated skin. In this case, the biophotonic material may be applied at regular intervals such as once a week, or at an interval deemed appropriate by the physician.

In the methods of the present disclosure, additional components may optionally be included in the biophotonic materials or used in combination with the biophotonic materials. Such additional components include, but are not limited to, healing factors, antimicrobials, oxygen-rich agents, wrinkle fillers such as botox, hyaluronic acid and polylactic acid, fungal, anti-bacterial, anti-viral agents and/or agents that promote collagen synthesis. These additional components may be applied to the skin in a topical fashion, prior to, at the same time of, and/or after topical application of the biophotonic materials of the present disclosure. Suitable healing factors comprise compounds that promote or enhance the healing or regenerative process of the tissues on the application site. During the photoactivation of a biophotonic material of the present disclosure, there may be an increase of the absorption of molecules of such additional components at the treatment site by the skin or the mucosa. In certain embodiments, an augmentation in the blood flow at the site of treatment can observed for a period of time. An increase in the lymphatic drainage and a possible change in the osmotic equilibrium due to the dynamic interaction of the free radical cascades can be enhanced or even fortified with the inclusion of healing factors. Healing factors may also modulate the biophotonic output from the biophotonic composition such as photobleaching time and profile, or modulate leaching of certain ingredients within the composition. Suitable healing factors include, but are not limited to glucosamines, allantoins, saffron, agents that promote collagen synthesis, anti-fungal, anti-bacterial, anti-viral agents and wound healing factors such as growth factors.

(i) Skin Rejuvenation

The biophotonic material of the present disclosure may be useful in promoting skin rejuvenation or improving skin condition and appearance. The dermis is the second layer of skin, containing the structural elements of the skin, the connective tissue. There are various types of connective tissue with different functions. Elastin fibers give the skin its elasticity, and collagen gives the skin its strength.

The junction between the dermis and the epidermis is an important structure. The dermal-epidermal junction interlocks forming finger-like epidermal ridges. The cells of the epidermis receive their nutrients from the blood vessels in the dermis. The epidermal ridges increase the surface area of the epidermis that is exposed to these blood vessels and the needed nutrients.

The aging of skin comes with significant physiological changes to the skin. The generation of new skin cells slows down, and the epidermal ridges of the dermal-epidermal junction flatten out. While the number of elastin fibers increases, their structure and coherence decreases. Also the amount of collagen and the thickness of the dermis decrease with the ageing of the skin.

Collagen is a major component of the skin's extracellular matrix, providing a structural framework. During the aging process, the decrease of collagen synthesis and insolubilization of collagen fibers contribute to a thinning of the dermis and loss of the skin's biomechanical properties.

The physiological changes to the skin result in noticeable aging symptoms often referred to as chronological-, intrinsic- and photo-ageing. The skin becomes drier, roughness and scaling increase, the appearance becomes duller, and most obviously fine lines and wrinkles appear. Other symptoms or signs of skin aging include, but are not limited to, thinning and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, a blotchy complexion.

The dermal-epidermal junction is a basement membrane that separates the keratinocytes in the epidermis from the extracellular matrix, which lies below in the dermis. This membrane consists of two layers: the basal lamina in contact with the keratinocytes, and the underlying reticular lamina in contact with the extracellular matrix. The basal lamina is rich in collagen type IV and laminin, molecules that play a role in providing a structural network and bioadhesive properties for cell attachment.

Laminin is a glycoprotein that only exists in basement membranes. It is composed of three polypeptide chains (alpha, beta and gamma) arranged in the shape of an asymmetric cross and held together by disulfide bonds. The three chains exist as different subtypes which result in twelve different isoforms for laminin, including Laminin-1 and Laminin-5.

The dermis is anchored to hemidesmosomes, specific junction points located on the keratinocytes, which consist of α-integrins and other proteins, at the basal membrane keratinocytes by type VII collagen fibrils. Laminins, and particularly Laminin-5, constitute the real anchor point between hemidesmosomal transmembrane proteins in basal keratinocytes and type VII collagen.

Laminin-5 synthesis and type VII collagen expression have been proven to decrease in aged skin. This causes a loss of contact between dermis and epidermis, and results in the skin losing elasticity and becoming saggy.

Recently another type of wrinkles, generally referred to as expression wrinkles, got general recognition. These wrinkles require loss of resilience, particularly in the dermis, because of which the skin is no longer able to resume its original state when facial muscles which produce facial expressions exert stress on the skin, resulting in expression wrinkles.

The biophotonic material of the present disclosure and methods of the present disclosure promote skin rejuvenation. In certain embodiments, the biophotonic material and methods of the present disclosure promote skin condition such as skin luminosity, reduction of pore size, reducing blotchiness, making even skin tone, reducing dryness, and tightening of the skin. In certain embodiments, the biophotonic material and methods of the present disclosure promote collagen synthesis. In certain other embodiments, the biophotonic material and methods of the present disclosure may reduce, diminish, retard or even reverse one or more signs of skin aging including, but not limited to, appearance of fine lines or wrinkles, thin and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, or a blotchy complexion. In certain embodiments, the biophotonic material and methods of the present disclosure may induce a reduction in pore size, enhance sculpturing of skin subsections, and/or enhance skin translucence.

In certain embodiments, the biophotonic material may be used in conjunction with collagen promoting agents. Agents that promote collagen synthesis (i.e., pro-collagen synthesis agents) include amino acids, peptides, proteins, lipids, small chemical molecules, natural products and extracts from natural products.

For instance, it was discovered that intake of vitamin C, iron, and collagen can effectively increase the amount of collagen in skin or bone. See, e.g., U.S. Patent Application Publication 20090069217. Examples of the vitamin C include an ascorbic acid derivative such as L-ascorbic acid or sodium L-ascorbate, an ascorbic acid preparation obtained by coating ascorbic acid with an emulsifier or the like, and a mixture containing two or more of those vitamin Cs at an arbitrary rate. In addition, natural products containing vitamin C such as acerola and lemon may also be used. Examples of the iron preparation include: an inorganic iron such as ferrous sulfate, sodium ferrous citrate, or ferric pyrophosphate; an organic iron such as heme iron, ferritin iron, or lactoferrin iron; and a mixture containing two or more of those irons at an arbitrary rate. In addition, natural products containing iron such as spinach or liver may also be used. Moreover, examples of the collagen include: an extract obtained by treating bone, skin, or the like of a mammal such as bovine or swine with an acid or alkaline; a peptide obtained by hydrolyzing the extract with a protease such as pepsin, trypsin, or chymotrypsin; and a mixture containing two or more of those collagens at an arbitrary rate. Collagens extracted from plant sources may also be used.

Additional pro-collagen synthesis agents are described, for example, in U.S. Pat. Nos. 7,598,291, 7,722,904, 6,203,805, 5,529,769, etc, and U.S. Patent Application Publications 20060247313, 20080108681, 20110130459, 20090325885, 20110086060, etc.

(ii) Skin Disorders

The biophotonic materials and methods of the present disclosure may be used to treat skin disorders that include, but are not limited to, erythema, telangiectasia, actinic telangiectasia, psoriasis, skin cancer, pemphigus, sunburn, dermatitis, eczema, rashes, impetigo, lichen simplex chronicus, rhinophyma, perioral dermatitis, pseudofolliculitis barbae, drug eruptions, erythema multiforme, erythema nodosum, granuloma annulare, actinic keratosis, purpura, alopecia areata, aphthous stomatitis, drug eruptions, dry skin, chapping, xerosis, ichthyosis vulgaris, fungal infections, herpes simplex, intertrigo, keloids, keratoses, milia, moluscum contagiosum, pityriasis rosea, pruritus, urticaria, and vascular tumors and malformations. Dermatitis includes contact dermatitis, atopic dermatitis, seborrheic dermatitis, nummular dermatitis, generalized exfoliative dermatitis, and statis dermatitis. Skin cancers include melanoma, basal cell carcinoma, and squamous cell carcinoma.

(iii) Acne and Acne Scars

The biophotonic materials and methods of the present disclosure may be used to treat acne. As used herein, "acne" means a disorder of the skin caused by inflammation of skin glands or hair follicles. The biophotonic materials and methods of the disclosure can be used to treat acne at early pre-emergent stages or later stages where lesions from acne are visible. Mild, moderate and severe acne can be treated with embodiments of the biophotonic compositions and methods. Early pre-emergent stages of acne usually begin with an excessive secretion of sebum or dermal oil from the sebaceous glands located in the pilosebaceous apparatus. Sebum reaches the skin surface through the duct of the hair follicle. The presence of excessive amounts of sebum in the duct and on the skin tends to obstruct or stagnate the normal flow of sebum from the follicular duct, thus producing a thickening and solidification of the sebum to create a solid plug known as a comedone. In the normal sequence of developing acne, hyperkeratinazation of the follicular opening is stimulated, thus completing blocking of the duct. The usual results are papules, pustules, or cysts, often contaminated with bacteria, which cause secondary infections. Acne is characterized particularly by the presence of comedones, inflammatory papules, or cysts. The appearance of acne may range from slight skin irritation to pitting and even the development of disfiguring scars. Accordingly, the biophotonic materials and methods of the present disclosure can be used to treat one or more of skin irritation, pitting, development of scars, comedones, inflammatory papules, cysts, hyperkeratinazation, and thickening and hardening of sebum associated with acne.

Some types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, and nodulocystic acne.

Some skin disorders present various symptoms including redness, flushing, burning, scaling, pimples, papules, pustules, comedones, macules, nodules, vesicles, blisters, telangiectasia, spider veins, sores, surface irritations or pain, itching, inflammation, red, purple, or blue patches or discolorations, moles, and/or tumors.

The biophotonic materials and methods of the present disclosure may be used to treat various types of acne. Some types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, and nodulocystic acne.

In certain embodiments, the biophotonic material of the present disclosure is used in conjunction with systemic or topical antibiotic treatment. For example, antibiotics used to treat acne include tetracycline, erythromycin, minocycline, doxycycline, which may also be used with the compositions and methods of the present disclosure. The use of the biophotonic material can reduce the time needed for the antibiotic treatment or reduce the dosage.

(iv) Wound Healing

The biophotonic materials and methods of the present disclosure may be used to treat wounds, promote wound healing, promote tissue repair and/or prevent or reduce cosmesis including improvement of motor function (e.g. movement of joints). Wounds that may be treated by the biophotonic materials and methods of the present disclosure include, for example, injuries to the skin and subcutaneous tissue initiated in different ways (e.g., pressure ulcers from extended bed rest, wounds induced by trauma or surgery, burns, ulcers linked to diabetes or venous insufficiency, wounds induced by conditions such as periodontitis) and with varying characteristics. In certain embodiments, the present disclosure provides biophotonic materials and methods for treating and/or promoting the healing of, for example, burns, incisions, excisions, lesions, lacerations, abrasions, puncture or penetrating wounds, surgical wounds, contusions, hematomas, crushing injuries, amputations, sores and ulcers.

Biophotonic materials and methods of the present disclosure may be used to treat and/or promote the healing of chronic cutaneous ulcers or wounds, which are wounds that have failed to proceed through an orderly and timely series of events to produce a durable structural, functional, and cosmetic closure. The vast majority of chronic wounds can be classified into three categories based on their etiology: pressure ulcers, neuropathic (diabetic foot) ulcers and vascular (venous or arterial) ulcers.

For example, the present disclosure provides biophotonic materials and methods for treating and/or promoting healing of a diabetic ulcer. Diabetic patients are prone to foot and other ulcerations due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. A patient with advanced neuropathy loses the ability to sense a sustained pressure insult, as a result, tissue ischemia and necrosis may occur leading to for example, plantar ulcerations. Microvascular disease is one of the significant complications for diabetics which may also lead to ulcerations. In certain embodiments, biophotonic materials and methods of treating a chronic wound are provided here in, where the chronic wound is characterized by diabetic foot ulcers and/or ulcerations due to neurologic and/or vascular complications of diabetes.

In other examples, the present disclosure provides biophotonic materials and methods for treating and/or promoting healing of a pressure ulcer. Pressure ulcers include bed sores, decubitus ulcers and ischial tuberosity ulcers and can cause considerable pain and discomfort to a patient. A pressure ulcer can occur as a result of a prolonged pressure applied to the skin. Thus, pressure can be exerted on the skin of a patient due to the weight or mass of an individual. A pressure ulcer can develop when blood supply to an area of the skin is obstructed or cut off for more than two or three hours. The affected skin area can turn red, become painful and necrotic. If untreated, the skin can break open and become infected. A pressure ulcer is therefore a skin ulcer that occurs in an area of the skin that is under pressure from e.g. lying in bed, sitting in a wheelchair, and/or wearing a cast for a prolonged period of time. Pressure ulcers can occur when a person is bedridden, unconscious, unable to sense pain, or immobile. Pressure ulcers often occur in boney prominences of the body such as the buttocks area (on the sacrum or iliac crest), or on the heels of foot.

Additional types of wounds that can be treated by the biophotonic materials and methods of the present disclosure include those disclosed by U.S. Pat. Appl. Publ. No. 20090220450, which is incorporated herein by reference.

There are three distinct phases in the wound healing process. First, in the inflammatory phase, which typically occurs from the moment a wound occurs until the first two to five days, platelets aggregate to deposit granules, promoting the deposit of fibrin and stimulating the release of growth factors. Leukocytes migrate to the wound site and begin to digest and transport debris away from the wound. During this inflammatory phase, monocytes are also converted to macrophages, which release growth factors for stimulating angiogenesis and the production of fibroblasts.

Second, in the proliferative phase, which typically occurs from two days to three weeks, granulation tissue forms, and epithelialization and contraction begin. Fibroblasts, which are key cell types in this phase, proliferate and synthesize collagen to fill the wound and provide a strong matrix on which epithelial cells grow. As fibroblasts produce collagen, vascularization extends from nearby vessels, resulting in granulation tissue. Granulation tissue typically grows from the base of the wound. Epithelialization involves the migration of epithelial cells from the wound surfaces to seal the wound. Epithelial cells are driven by the need to contact cells of like type and are guided by a network of fibrin strands that function as a grid over which these cells migrate. Contractile cells called myofibroblasts appear in wounds, and aid in wound closure. These cells exhibit collagen synthesis and contractility, and are common in granulating wounds.

Third, in the remodeling phase, the final phase of wound healing which can take place from three weeks up to several years, collagen in the scar undergoes repeated degradation and re-synthesis. During this phase, the tensile strength of the newly formed skin increases.

However, as the rate of wound healing increases, there is often an associated increase in scar formation. Scarring is a consequence of the healing process in most adult animal and human tissues. Scar tissue is not identical to the tissue which it replaces, as it is usually of inferior functional quality. The types of scars include, but are not limited to, atrophic, hypertrophic and keloidal scars, as well as scar contractures. Atrophic scars are flat and depressed below the surrounding skin as a valley or hole. Hypertrophic scars are elevated scars that remain within the boundaries of the original lesion, and often contain excessive collagen arranged in an abnormal pattern. Keloidal scars are elevated scars that spread beyond the margins of the original wound and invade the surrounding normal skin in a way that is site specific, and often contain whorls of collagen arranged in an abnormal, fashion.

In contrast, normal skin consists of collagen fibers arranged in a basket-weave pattern, which contributes to both the strength and elasticity of the dermis. Thus, to achieve a smoother wound healing process, an approach is needed that not only stimulates collagen production, but also does so in a way that reduces scar formation.

The biophotonic materials and methods of the present disclosure promote the wound healing by promoting the formation of substantially uniform epithelialization; promoting collagen synthesis; promoting controlled contraction; and/or by reducing the formation of scar tissue. In certain embodiments, the biophotonic materials and methods of the present disclosure may promote wound healing by promoting the formation of substantially uniform epithelialization. In some embodiments, the biophotonic materials and methods of the present disclosure promote collagen synthesis. In some other embodiments, the biophotonic materials and methods of the present disclosure promote controlled contraction. In certain embodiments, the biophotonic materials and methods of the present disclosure promote wound healing, for example, by reducing the formation of scar tissue.

In the methods of the present disclosure, the biophotonic materials of the present disclosure may also be used in combination with negative pressure assisted would closure devices and systems.

In certain embodiments, the biophotonic material is kept in place for up to one, two or 3 weeks, and illuminated with light which may include ambient light at various intervals. In this case, the composition may be covered up in between exposure to light with an opaque material or left exposed to light.

(6) Kits

The present disclosure also provides kits for preparing a biophotonic material and/or providing any of the components required for forming biophotonic materials of the present disclosure.

In some embodiments, the kit includes containers comprising the components or compositions that can be used to make the biophotonic materials of the present disclosure. In some embodiments, the kit includes a biophotonic material of the present disclosure. The different components making up the biophotonic materials of the present disclosure may be provided in separate containers. For example, if the biophotonic material is to include an oxygen-rich agent, the oxygen-rich agent is preferably provided in a container separate from the chromophore. Examples of such containers are dual chamber syringes, dual chamber containers with removable partitions, sachets with pouches, and multiple-compartment blister packs. Another example is one of the components being provided in a syringe which can be injected into a container of another component.

In other embodiments, the kit comprises a systemic drug for augmenting the treatment of the biophotonic material of the present disclosure. For example, the kit may include a systemic or topical antibiotic, hormone treatment (e.g. for acne treatment or wound healing), or a negative pressure device.

In certain embodiments, the kit comprises a first component comprising a first chromophore; and a second component comprising at least one thickening agent, wherein the thickening agent can form a cohesive matrix when mixed with the first component, when the mixture is applied to skin, or when illuminated with light.

In other embodiments, the kit comprises a means for applying the components of the biophotonic materials.

In certain aspects, there is provided a container comprising a chamber for holding a biophotonic material, and an outlet in communication with the chamber for discharging the biophotonic material from the container, wherein the biophotonic material comprises at least one chromophore in a carrier medium which can form a biophotonic material after being discharged from the sealed chamber, for example on contact with skin or on illumination with a light. The container can be a pressurized or non-pressurized spray can.

In certain embodiments, the kit comprises a first component comprising the biophotonic material or a non-cohesive form of the biophotonic material ('precursor'), and the second component comprises a dressing or a mask. The dressing or mask may be a porous or semi-porous structure for receiving the biophotonic material. The dressing or mask may also comprise woven or non-woven fibrous materials. The biophotonic material or its precursor can be incorporated, such as by injection, into the dressing before the biophotonic material takes on a cohesive form within the dressing or mask.

In certain embodiments of the kit, the kit may further comprise a light source such as a portable light with a wavelength appropriate to activate the chromophore the biophotonic material. The portable light may be battery operated or re-chargeable.

Written instructions on how to use the biophotonic materials in accordance with the present disclosure may be included in the kit, or may be included on or associated with the containers comprising the compositions or components making up the biophotonic materials of the present disclosure. The instructions can include information on how to form the cohesive matrix from the thickening agent(s) or matrix precursors provided with the kit.

Identification of equivalent biophotonic materials, methods and kits are well within the skill of the ordinary practitioner and would require no more than routine experimentation, in light of the teachings of the present disclosure.

Variations and modifications will occur to those of skill in the art after reviewing this disclosure. The disclosed features may be implemented, in any combination and subcombinations (including multiple dependent combinations and sub-combinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

Practice of the disclosure will be still more fully understood from the following examples, which are presented herein for illustration only and should not be construed as limiting the disclosure in any way.

EXAMPLES

Example 1—Preparation of an Exemplary Cohesive Biophotonic Material

A cohesive biophotonic material was prepared according to an embodiment of the present disclosure and as summarized in Table 1.

TABLE 1

Composition of a cohesive biophotonic material according to an embodiment of the present disclosure.

| Ingredients | % in composition (wt/wt) |
| --- | --- |
| Water | 60-95 |
| Glycerine | 5-15 |
| Propylene Glycol | 2-6 |
| Sodium hyaluronate | 2-8 |
| Urea peroxide | 1-5 |
| Glucosamine sulfate | 0.5-4 |
| Carbopol | 0.1-2 |
| First Chromophore | 0.001-0.01 |
| Second chromophore | 0.001-0.01 |

Figure 3:
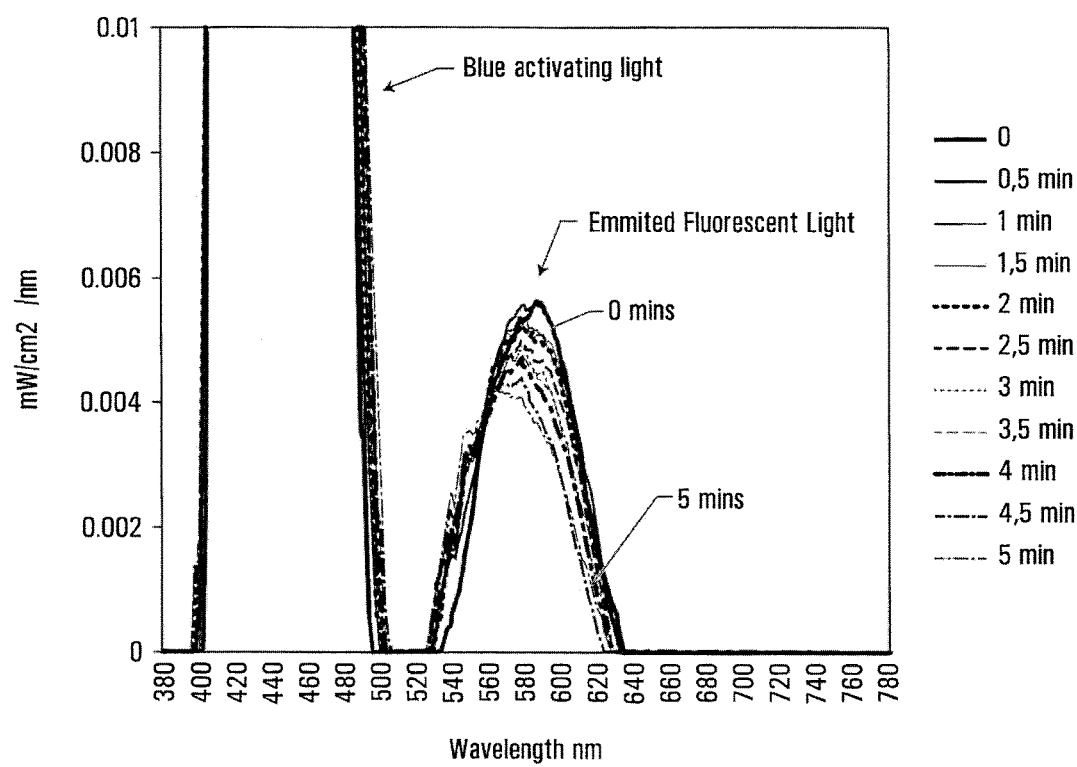
FIG. 3 is an emission fluorescence spectrum from an activated biophotonic material according to an embodiment of the present disclosure (Example 1).

Phase A was prepared by mixing water, Eosin Y, Rose Bengal and glucosamine sulphate. Phase B (water, glycerine, propylene glycol, urea peroxide, carbopol) was then added to Phase A, and mixed until a light viscous liquid was obtained. Phase C (sodium hyaluronate) was then added to the mixture, and mixed until a homogenous thick cohesive gel was obtained. This cohesive homogenous gel was spread onto a flat surface, covered with an aluminum sheet and allowed to dry for 24 hours. After 24 hours, the resulting membrane was, easy to manipulate, and could be applied to the skin and peeled off with little or no residue remaining. A 5-20% weight loss of the total weight of the material was found to occur after drying for 24 hours. The membrane could be stored between two layers of saran wrap, paraffin etc. On illumination with light (peak wavelength between 400-470 nm and a power density of about 30-150 mW/cm$^2$) for 5 minutes at a distance of 5 cm from the light source, the film emitted fluorescent light which was captured by a photospectrometer (SP-100 spectroradiometer (SP-100, ORB Optronix) to measure the power density spectra versus wavelength and is illustrated in FIG. 3. The emitted fluorescent light was in the green, yellow and orange portions of the electromagnetic spectrum. An at least partial photobleaching of the chromophores was observed after 5 minutes of illumination.

Example 2—Angiogenic Potential of a Biophotonic Composition

The angiogenic potential of a biophotonic composition was evaluated using a human skin model containing fibroblasts and keratinocytes. The composition was a transparent gel comprising fluorescent chromophores, Eosin Y and Erythrosine. Briefly, the biophotonic composition was placed on top of the human skin model such that they were separated by a nylon mesh of 20 micron pore size. The composition was then irradiated with blue light ('activating light') for 5 minutes at a distance of 10 cm from the light source. The activating light consisted of light emitted from an LED lamp having an average peak wavelength of about 400-470 nm and a power density of about 30-150 mW/cm². At a 10 cm distance from the LEDs, the activating light had a power at the peak wavelength of about 2-3 mW/cm²/nm (about 2.5 mW/cm²/nm), an average power of about 55-65 mW/cm², and a fluence in 5 minutes of irradiation of about 15-25 J/cm² (about 16-20 J/cm²). Upon illumination with the activating light, the biophotonic composition emitted fluorescent light, as measured using a SP-100 spectroradiometer (SP-100, ORB Optronix) and illustrated in FIG. 4. As the composition allowed the activating light to pass therethrough, the skin model was illuminated substantially simultaneously by both the activating light and the fluorescent light.

Since the biophotonic composition was in limited contact with the cells, the fibroblasts and keratinocytes were exposed mainly to the activating light and the fluorescent light emitted from the biophotonic composition. Conditioned media from the treated human 3D skin model were then applied to human aortic endothelial cells and diseased microvascular endothelial cells from diabetic patients previously plated in Matrigel™. The formation of tubes by endothelial cells was observed and monitored by microscopy after 24 hours. The conditioned medium from 3D skin models treated with light illumination induced endothelial tube formation in vitro, suggesting an indirect effect of the light treatment (blue light and fluorescence) on angiogenesis via the production of factors by fibroblasts and keratinocytes. Plain medium and conditioned medium of untreated skin samples were used as a control, and did not induce endothelial tube formation.

Figure 4:
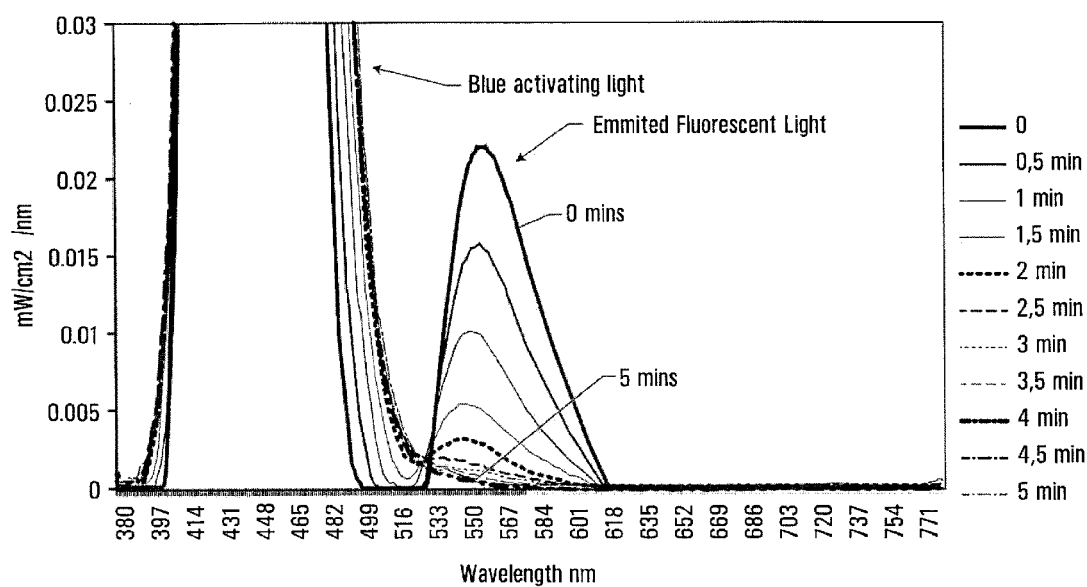
FIG. 4 is an emission fluorescence spectrum from a photoactivated biophotonic material irradiating fibroblasts and keratinocytes for evaluating protein regulation and gene expression (Example 2).

Example 3—Protein Secretion and Gene Expression Profiles of a Biophotonic Composition Wounded and unwounded 3D human skin models (EpiDermFT™, MatTek Corporation) were used to assess the potential of a composition to trigger distinct protein secretion and gene expression profiles. The biophotonic composition comprised fluorescent chromophores Eosin Y and Erythrosine. The composition was placed on top of wounded and unwounded 3D human skin models cultured under different conditions (with growth factors, 50% growth factors and no growth factors). The skin models and the composition were separated by a nylon mesh of 20 micron pore size. Each skin model-composition combination was then irradiated with blue light ('activating light') for 2 minutes by light having a profile similar to that described in Example 2. The fluorescence emission is shown in FIG. 4. The controls consisted of 3D skin models not illuminated with light.

Gene expression and protein secretion profiles were measured 24 hours post-light exposure. Cytokine secretion was analyzed by antibody arrays (RayBio Human Cytokine antibody array), gene expression was analyzed by PCR array (PAHS-013A, SABioscience) and cytotoxicity was determined by GAPDH and LDH release. Results (Tables 2 and 3) showed that the light treatment is capable of increasing the level of protein secreted and gene expression involved in the early inflammatory phase of wound healing in wounded skin inserts and in non-starvation conditions. Interestingly, the effect of the light treatment on unwounded skin models has a much lower impact at the cellular level than on wounded skin insert, which suggests an effect at the cellular effect level of the light treatment. It seems to modulate the mediators involved in inflammation. Cytotoxicity was not observed in the light treatments.

TABLE 2

List of proteins with statistically significant difference secretion ratio between treated and untreated control at day 3.

| | Medium 1× | Medium 0.5× | Medium 0× |
|---|---|---|---|
| Increase | | ENA78 p = 0.04 ↑↑ | Angiogenin p = 0.03 ↑ |
| | | Il-1R4/ST2 p = 0.02 ↑↑ | CXCL16 p = 0.04 ↑ |
| | | MMP3 p = 0.01 ↑↑ | |
| | | MCP-2 p = 0.04 ↑↑ | |
| Decrease | BMP6 p = 0.01 ↓ | BMP6 p = 0.02 ↓ | |
| | TNFα p = 0.005 ↓ | | |

Two arrows mean that the ratio was over 2 folds.

TABLE 3

List of genes with statistically significant difference expression ratio between treated and untreated control during the first 24 hours.

| | Medium 1× | Medium 0.5× | Medium 0× |
|---|---|---|---|
| Increase | CTGF ↑<br>p = 0.02 | CTGF ↑<br>P = 0.04 | MMP3 ↑↑<br>p = 0.007 |
| | ITGB3 ↑<br>p = 0.03 | ITGB3 ↑<br>p = 0.05 | LAMA1 3 ↑<br>p = 0.0 |
| | MMP1 ↑<br>p = 0.03 | MMP1 ↑↑<br>p = 0.02 | ITGA2 ↑<br>p = 0.03 |
| | MMP3 ↑<br>p = 0.01 | MMP10 ↑↑<br>p = 0.003 | |
| | THBS1 ↑<br>P = 0.02 | MMP3 ↑↑<br>p = 0.007 | |
| | | MMP8 ↑↑<br>p = 0.02 | |
| | | THBS1 ↑<br>p = 0.03 | |
| Decrease | HAS1 ↓↓<br>p = 0.009 | NCAM1 ↓↓<br>p = 0.02 | |
| | NCAM1 ↓↓<br>p = 0.05 | VCAN ↓<br>p = 0.02 | |
| | VCAM1 ↓↓<br>p = 0.03 | LAMC1 ↓<br>p = 0.002 | |
| | COL7A1 ↓<br>p = 0.04 | COL6A1 ↓<br>p = 0.007 | |
| | CTNNA1 ↓<br>p = 0.03 | MMP7 ↓<br>p = 0.003 | |

Two arrows mean that the ratio was over 2 folds.

Example 4—Selecting Concentration of Chromophore in Composition

Figure 5A:
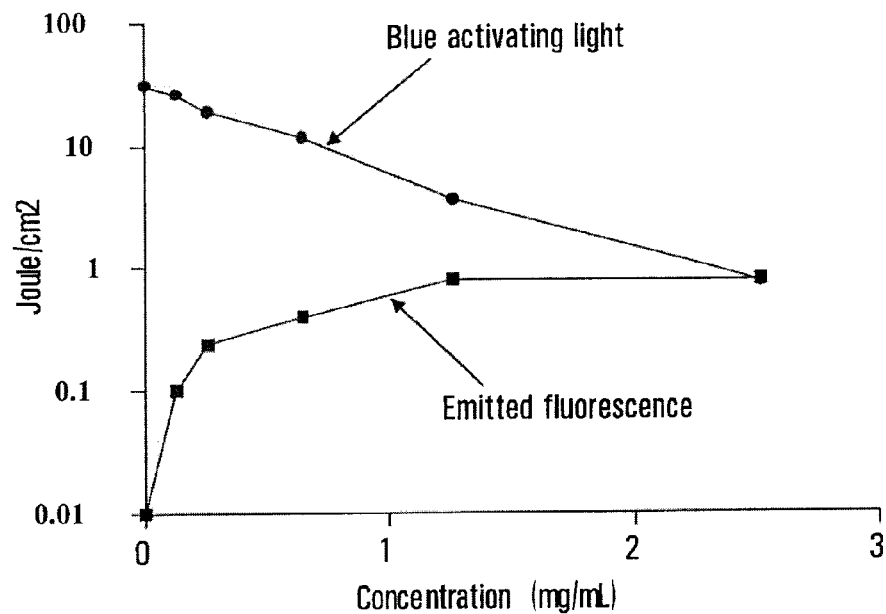
FIGS. 5a and 5b are emission fluorescence spectra for Eosin Y and Fluorescein, respectively, and the activating light passing through the composition, at different concentrations of the chromophores (Example 4).
Figure 5B:
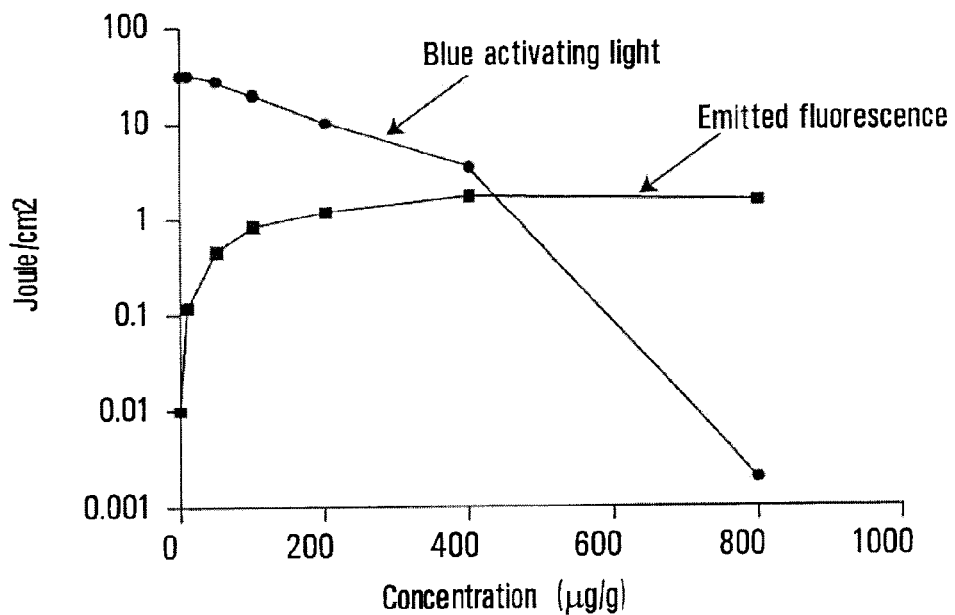

The fluorescence spectra of biophotonic materials with different concentrations of chromophores were investigated using a spectrophotometer and an activating blue light. Exemplary fluorescence spectra of Eosin Y and Fluorescein are presented in FIGS. 5a and 5b, respectively. It was found that emitted fluorescence from the chromophores increase rapidly with increasing concentration but slows down to a plateau with further concentration increase. Activating light passing through the composition decreases with increasing chromophore composition as more light is absorbed by the chromophores. Therefore, the concentration of chromophores in biophotonic materials of the present disclosure can be selected according to a required ratio and level of activating light and fluorescence treating the tissue based on this example. The thickness of the biophotonic material can also be modulated to control the light treating the tissues, as well as the optical properties of the composition such as transparency.

Example 5—Synergistic Combination of Eosin Y and Fluorescein

Figure 6A:
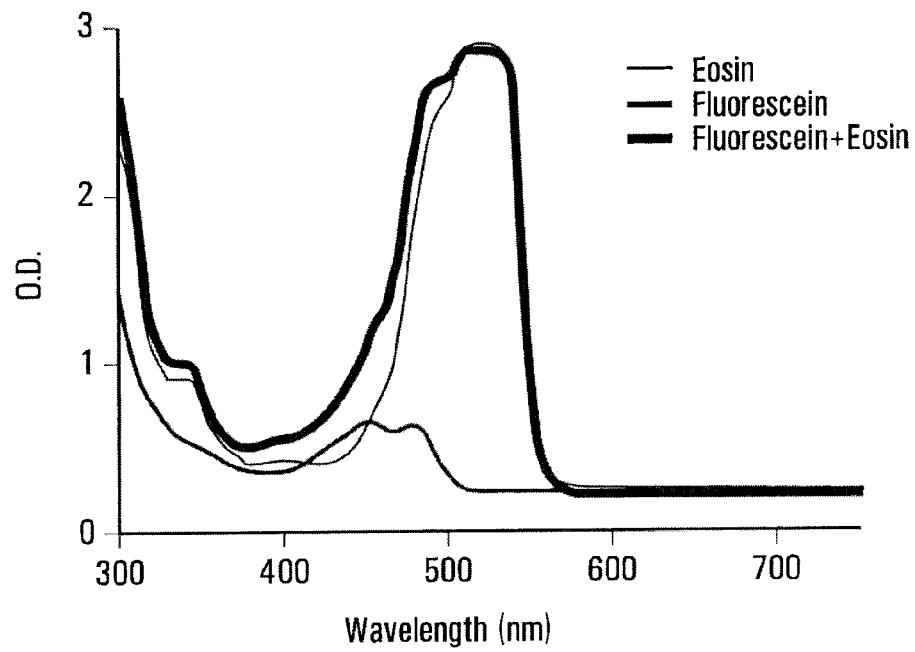
FIGS. 6a and 6b are absorbance and emission spectra, respectively, of Eosin and Fluorescein in a gel (Example 5).
Figure 6B:
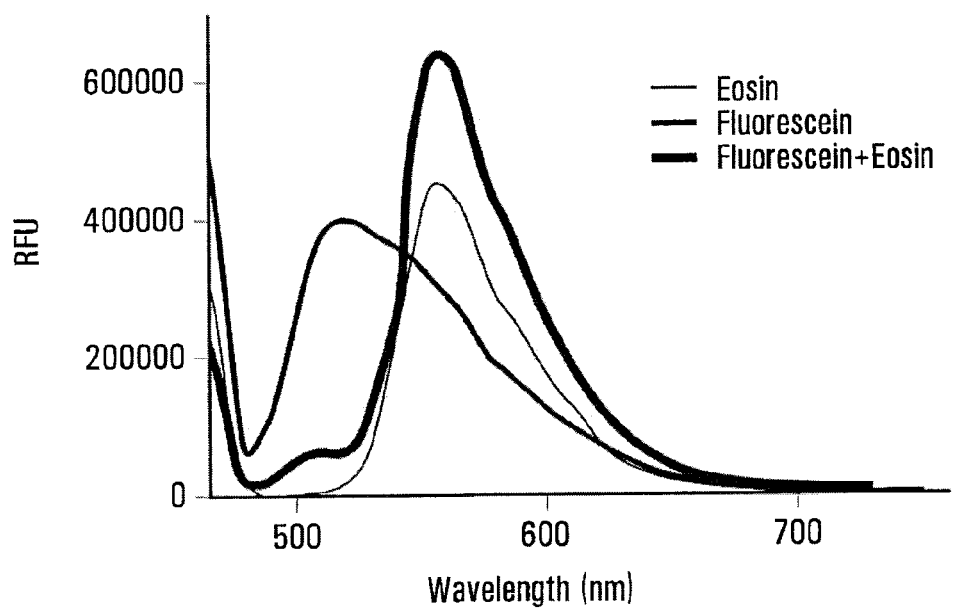

The photodynamic properties of (i) Fluorescein sodium salt at about 0.09 mg/mL, (ii) Eosin Y at about 0.305 mg/mL, and (iii) a mixture of Fluorescein sodium salt at about 0.09 mg/mL and Eosin Y at about 0.305 mg/mL in a gel (comprising about 12% carbamide peroxide), were evaluated. A flexstation 384 II spectrometer was used with the following parameters: mode fluorescence, excitation 460 nm, emission spectra 465-750 nm. The absorption and emission spectra are shown in FIGS. 6a and 6b, respectively, which indicate an energy transfer between the chromophores in the combination. It is to be reasonably inferred that this energy transfer can also occur in biophotonic materials of the present disclosure.

Example 6—Synergistic Combination of Eosin Y, Fluorescein and Rose Bengal

Figure 7A:
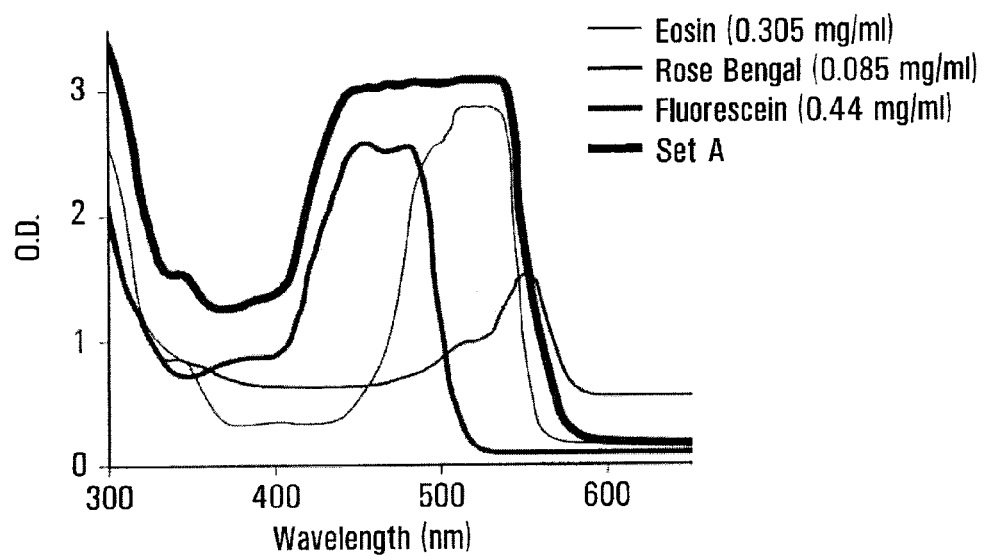
FIGS. 7a and 7b are absorbance and emission spectra, respectively, of Eosin, Fluorescein and Rose Bengal in a gel (Example 6).
Figure 7B:
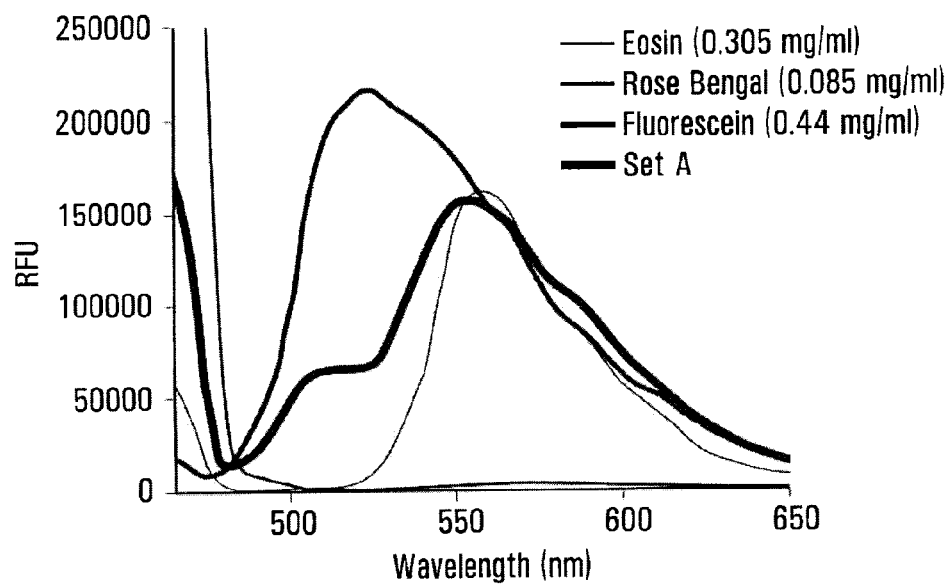

The photodynamic properties of (i) Rose Bengal at about 0.085 mg/mL, (ii) Fluorescein sodium salt at about 0.44 mg/mL final concentration, (ii) Eosin Y at about 0.305 mg/mL, and (iii) a mixture of (i), (ii) and (iii) in a gel (comprising about 12% carbamide peroxide) (Set A), were evaluated. A flexstation 384 II spectrometer was used with the following parameters: mode fluorescence, excitation 460 nm, emission spectra 465-750 nm. The absorbance and emission spectra are shown in FIGS. 7a and 7b, respectively, which indicate an energy transfer between the chromophores in the chromophore combination. It is to be reasonably inferred that this energy transfer can also occur in biophotonic materials of the present disclosure.

Energy transfer was also seen between: Eosin Y and Rose Bengal; Phloxine B and Eosin Y; Phloxine B, Eosin Y and Fluorescein, amongst other combinations. It is to be reasonably inferred that energy transfer can also occur in biophotonic materials of the present disclosure.

Example 7—Collagen Formation Potential of a Biophotonic Composition

A biophotonic composition comprising 0.01% Eosin Y and 0.01% Fluorescein in a carrier matrix (1.8% carbopol gel) was evaluated for its potential to induce collagen formation. Dermal human fibroblasts were plated in glass-bottomed dishes with wells (MatTek®). There were approximately 4000 cells per well. After 48 hours, the glass-bottomed dishes were inverted and the cells were treated through the glass bottom with (i) no light (control), (ii) sunlight exposure for about 13 minutes at noon (control), (iii) the composition applied to the glass well bottom on the other side of the cells (no light exposure), (iv) the composition applied to the glass well bottom on the other side of the cells and exposed to sunlight for about 13 minutes at noon, and (v) the composition applied to the glass well bottom on the other side of the cells and illuminated with blue light. In the case of (iii), (iv) and v), there was no direct contact between the cells and the composition. In the case of (iv), the cells were exposed to emitted light from and through the Eosin Y and Fluorescein composition when exposed to sunlight. A partial photobleaching was observed in (iv) and total photobleaching in (v). After the treatment, the cells were washed and incubated in regular medium for 48 hours. A collagen assay was then performed on the supernatant using the Picro-Sirius red method. This involved adding Sirius red dye solution in picric acid to the supernatant, incubating with gentle agitation for 30 minutes followed by centrifugation to form a pellet. The pellet was washed first with 0.1N HCl and then 0.5 N NaOH to remove free dye. After centrifugation, the suspension was read at 540 nm for collagen type I. The results are shown in Table 4.

TABLE 4

A qualitative comparison of collagen type I concentration in a dermal human fibroblast supernatant exposed to (i) no light (control), (ii) sunlight exposure for about 13 minutes at noon (control), (iii) any light emitted from the Eosin Y and Fluorescein composition through a glass separation (no activating light exposure), (iv) any light emitted from and through the Eosin Y and Fluorescein composition through a glass separation when illuminated with sunlight exposure for about 13 minutes at noon, and (v) light emitted from and through the composition through a glass separation when illuminated with blue light.

| | No light (control) | Sunlight alone (alone) | Eosin Y and Fluorescein- no light | Eosin Y and Fluorescein- sunlight | Eosin Y and Fluorescein- blue light |
|---|---|---|---|---|---|
| Collagen formation | + | + | ++ | +++ | +++ |

++ indicates collagen levels about twice as high as +,
+++ indicates collagen levels about three times as high as +.

There was a statistical difference between the collagen levels induced by the Eosin Y and Fluorescein composition exposed to sunlight compared to the no light and sunlight alone controls. There was also a statistical difference between the collagen levels induced by composition exposed to blue light compared to the no light and sunlight alone controls. Collagen generation is indicative of a potential for tissue repair including stabilization of granulation tissue and decreasing of wound size. It is also linked to reduction of fine lines, a decrease in pore size, improvement of texture and improvement of tensile strength of intact skin.

It is to be reasonably expected that the same or similar biophotonic effects can be obtained with a cohesive biophotonic material of the present disclosure providing substantially similar or equivalent light emission properties as the compositions described in Examples 2, 3 and 7.

Example 8—Preparation of an Exemplary Cohesive Biophotonic Material Based on Silicone Cohesive biophotonic membranes were made, according to embodiments of the present disclosure, comprising a silicone membrane having incorporated therein chromophores, specifically water soluble chromophores Eosin Y and Fluorescein. The biophotonic membranes were based on a colloidal system comprising an aqueous phase of solubilized chromophores within a solid silicone phase (microemulsion). The cohesive biophotonic membrane was made by mixing a base (B) comprising (i) dimethyl siloxane, dimethylvinyl terminated, (ii) dimethylvinylated and trimethylated silica, and (iii) tetra (trimethoxysiloxy) silane in ethyl benzene and with a curing agent (C) comprising (i) dimethyl, methylhydrogen siloxane, (ii) dimethyl siloxane, dimethylvinyl terminated, (iii) dimethylvinylated and trimethylated silica, and (iv) tetramethyl tetravinyl cyclotetra siloxane in ethyl benzene (both in liquid form from a Sylgard® 184 silicone elastomer kit, Dow Corning Corp, Ltd). When mixed at a ratio of 10 (B):1 (C), the mixture cures to an elastic material. The material obtained was a flexible and transparent/translucent elastomer. A stabilizing agent was also used to stabilize the emulsion and avoid phase separation. In one example, carboxymethyl cellulose (CMC) was used as the stabilizing agent (about 2%). In another example, gelatin was used as the stabilizing agent.

In one embodiment, 9.4 g of the base was mixed with 0.94 g of the curing agent, and to this was added 2 mL of 2% CMC solution (18 wt %) containing 0.327 mg (0.011 wt % within the aqueous phase) of Eosin Y and 0.327 mg (0.011 wt % within the aqueous phase) of Fluorescein. The whole mixture was emulsified vigorously for about 15 minutes and cast on a petri dish for curing at 35° C. for about 16 hours forming a translucent/transparent membrane comprising a silicone matrix with embedded droplets of the chromophore in CMC phase. In another embodiment, 2 mL of gelatin solution (5%) was used as the stabilizing agent instead of CMC. This also formed a translucent/transparent membrane comprising a silicone matrix with embedded droplets of the chromophores in the gelatin phase. In both cases, a 2 mm thick membrane was achieved, although it will be understood that the thickness of the membrane can be controlled by the volume of cast solution. In both cases, the membranes could be applied and removed from tissue (human skin) in one piece.

It will be appreciated that other stabilizing agents which can be used which include but are not limited to methyl cellulose or hydroxyethylcellulose. Other concentrations of gelatin can be used such as from about 1 to about 20 wt %. The total weight percent of the aqueous phase can range from about 2 weight % to about 40 weight %.

When the biophotonic membranes were illuminated with blue light, the chromophores absorbed and emitted light. An at least partial photobleaching of the chromophores was observed with time of illumination. When the water soluble fluorescent chromophores were incorporated directly into the silicone (i.e. as a single phase), they did not absorb or emit light. It is believed by the inventors that their inclusion in the silicone membrane as an aqueous phase provided the appropriate medium to allow biophotonic activity. Instead of a liquid phase, the water soluble chromophores could also be directly surrounded by any other medium which allows the absorption and emission of light, such as a gel or water, or adsorbed on fine solid particles such as, but not limited to, silica and hydroxyapatite particles.

The above example can also be demonstrated using any other liposoluble polymers or matrices, instead of silicone.

Example 9—Preparation of an Exemplary Cohesive Biophotonic e Ial Based on Gelatin A cohesive biophotonic material was made, according to another embodiment of the present disclosure, comprising a cohesive gelatin matrix incorporating therein chromophores. In a typical preparation, 10 g of gelatin was dispersed in 50 mL of de-ionized water then heated to around 65° C. in a hot water bath under continuous stirring until complete dissolution of gelatin. While the temperature was decreased to around 40° C., 0.5 mL of Eosin Y solution (10.9 mg/mL) was added to the gelatin solution, and the resulting gelatin solution (20% w/v) including Eosin Y was cast on a petridish and cooled down to room temperature to form a hydrogel membrane of gelatin containing Eosin Y. A transparent elastic membrane of 2 mm was obtained. The membrane could be applied and removed from tissue in one piece. When the gelatin membrane was illuminated with blue light, the chromophore absorbed and emitted light. An at least partial photobleaching of the chromophore within the cohesive membrane was observed after illumination. A similarly peelable membrane was also obtained with a gelatin matrices having more than 5 wt %. Peelable biophotonic membranes having <about 5 weight % gelatin could be obtained by adding chemical cross-linkers such as glutaraldehyde or glyoxal. Similar results were also obtained using chitosan as the cohesive matrix instead of gelatin.

Example 10—Measurement of Tensile Strength

The tensile strength of certain embodiments of the silicone and gelatin-based cohesive biophotonic materials formed according to Examples 8 and 9 were measured according to the following method. Rectangular test samples of 50 mm×10 mm having a 2 mm thickness were prepared based on the silicone and gelatin membranes of Examples 8 and 9 as well the membranes without chromophore(s). Sample length, width and thickness were verified at 3 points per dimension using a Vernier caliper and were used to calculate the cross-section area of the samples.

Each end of the sample was tightly fixed between a clamp with a 15 mm rubber grip linked to a $\frac{1}{16}$" steel cable. This sample/clamp assembly was installed vertically in a rigid scaffold made of steel tubes. The top cable was hung from a manual ratcheting device for winching the top cable away from the bottom cable, and the bottom cable was attached to a weight. The weight was loaded on a precision balance which was installed vertically under the manual ratcheting device. The sample between the clamps was then stretched at a steady slow rate using the winch. The force required to deform the sample was measured by the decrease of weight measured on the balance relative to a baseline length. The baseline was measured by relaxing the sample so that the weight measured by the balance was maximal. The top cable was then pulled away from the bottom cable via the ratcheting mechanism until a weight decrease was observed on the scale. This point was considered baseline and the reading on the balance was recorded and the length of the sample (distance between the clamps) was measured with a Vernier caliper. This length was defined as the initial length of the sample. The ratchet was then activated stepwise to stretch the sample with the balance reading and sample length being recorded at every step until rupture of the sample. Absence of grip slippage was verified by checking the stabilization of the measured weight and using visual indicators on the samples.

Figure 8A:
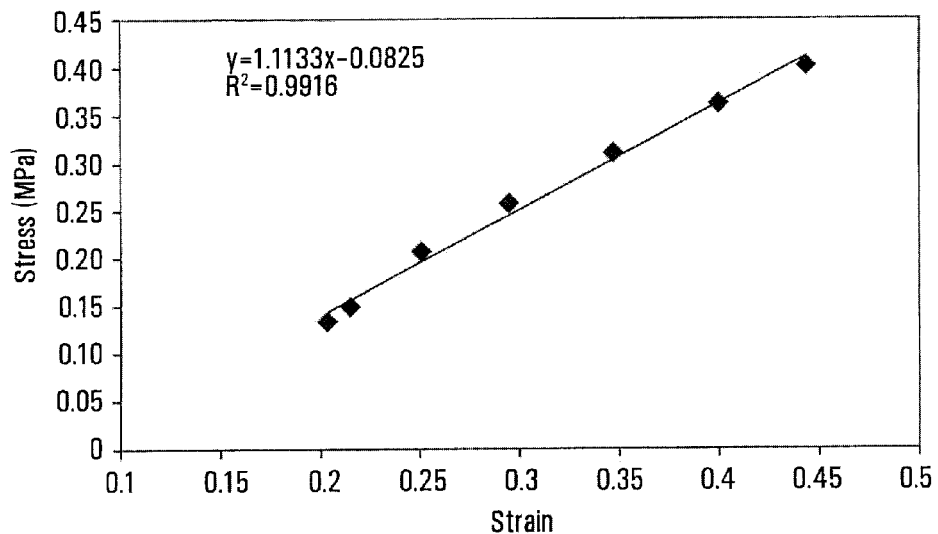
FIGS. 8a and 8b are stress-strain curves of cohesive biophotonic materials according to embodiments of the present disclosure (Example 10).
Figure 8B:
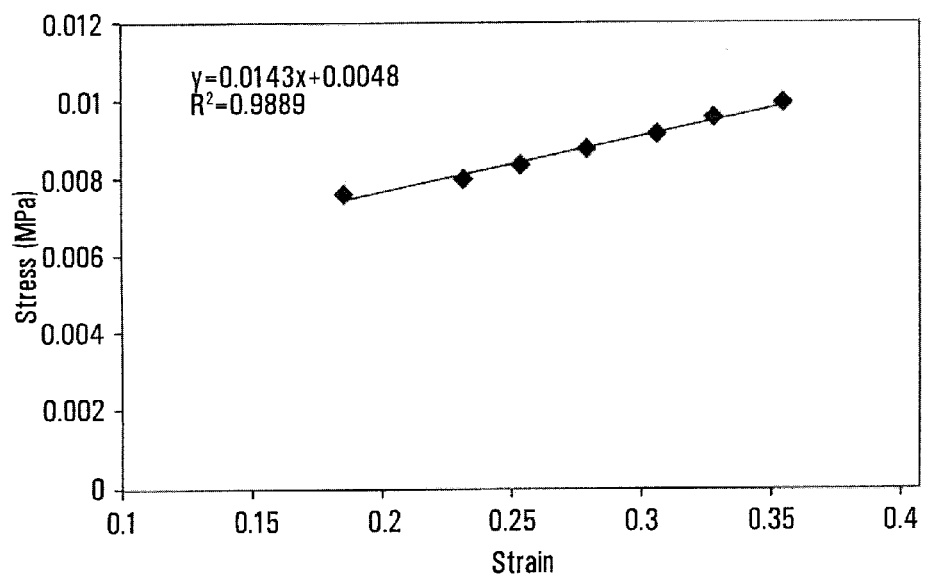

Typical stress-strain curves for the silicone-based and the gelatin-based membranes are shown in FIGS. 8a and 8b, respectively. The silicone membranes with and without chromophores, and with different thickening agents, had substantially similar tensile properties. The gelatin membranes with and without chromophores also had substantially similar tensile properties. The gelatin-based membranes had a tensile strength of about 0.01 MPa (±10%) (100 kPa) and an Elastic Modulus (slope of the stress/strain curve) of about 0.01 MPa (±10%) (100 kPa). The silicone-based membranes were stiffer than the gelatin-based membranes and had an average Elastic Modulus of about 1.11 MPa (±10%) (1110 kPa). This was well within the range reported in literature of about 1.2-1.8 MPa) The measured tensile strength was 0.405 MPa (826 g) due to grip slippage but is expected to be up to about 8 MPa based on literature reports on cured silicone.

This methodology was based on a similar principle of operation as American Society for Testing and Materials tensile testing methods such as ASTM D638, ASTM D882 and ASTM D412. However, instead of a pneumatic force, in the present example, gravity was used for sample extension.

Example 11—Measurement of Adhesion Strength

The adhesion strength of certain embodiments of the biophotonic materials formed according to Examples 8 and 9 were measured according to the following method. Samples were prepared as described in Example 10. One end of each sample was fixed to a clamp with a 15 mm rubber grip linked to one end of a 1/16" steel cable. The other end of the cable, via a low-friction pulley, was attached to a weight placed on a balance. The sample was laid flat on the skin of an inside forearm of a volunteer. A known weight, of surface area matching the sample, was then placed on the sample in order to apply a homogenous and known downwards force on the sample contacting the skin. The normal force $F_n$, (force exerted by each surface on the other in a perpendicular direction to the surface) was calculated by multiplying the combined weight of the sample and the weight on the sample by the gravity constant, g (9.8 m/s$^2$). The forearm, with the sample loaded with the weight, was then pulled away from the cable until the sample slipped from the skin surface. The weight recorded on the balance at this time was calculated by multiplying g to obtain the force of friction (Fr) (force required to overcome the friction between the sample and the skin). The friction coefficient of the sample can then be calculated using $F_f \leq \mu F_n$ (Coulomb's friction law).

On average, the silicone-based membranes had a friction coefficient of about 1.43, and the gelatin-based membranes had a friction coefficient of about 1.04. These values can be converted to the weight required to shear off a sample from the test surface by multiplying the friction coefficient by the sample weight. So, for the silicone-based membranes, a weight of 1.50 g is required to shear-off the membranes from skin. From FIG. 8a, this is equivalent to an elongation of about 0.1% and is well below its tensile strength. For the gelatin-based membranes, a weight of about 1.04 g was required to shear-off the membranes from skin. From FIG. 8b, this is equivalent to an elongation of about 1.5% and is well below its tensile strength (equivalent to 24.12 g). Therefore, all the silicone-based membranes and gelatin-based membranes of Examples 8 and 9 were peelable.

Example 12—Demonstration of Peelable Nature of Cohesive Biophotonic Materials of the Present Disclosure The biophotonic materials described in Examples 1, 8 and 9 were evaluated for peelability by applying them to the skin of volunteers and peeling off by hand. All membranes could be peeled off, reapplied and peeled off again without damage to the membranes and without leaving residues on the volunteer skins.

Example 13—Cell Studies

Certain embodiments of the cohesive biophotonic materials of Example 8 were evaluated for their ability to modulate inflammation, specifically cytokines IL6 and IL8. HaCaT cells were used as an accepted in vitro module for assessing modulation of these inflammatory cytokines. A non-toxic concentration of IFNI was used to modulate the secretion of IL6 and IL8 by the HaCaT cells.

Silicone membranes containing an aqueous phase of Eosin Y and Fluorescein and including either CMC or gelatin in the aqueous phase were evaluated. The anti-inflammatory effect of Dexamethasone was used as a positive control at a concentration of 5 µM. The materials were illuminated with blue light for 90 seconds at a distance of 5 cm at a fluence of about 11.5 J/cm$^2$. Cytokine quantification was performed by cytokine ELISA on the culture supernatant 24 hours after treatment. The quantity of cytokine secreted was normalized to cell viability. No toxic effect was observed for all the test samples as measured by cell viability using a spectrophotometric evaluation of viable cell number 24 hours after treatment. All of the membranes tested, produced a downward modulation of 1L6 and 1L8 on IFIγ stimulated HaCaT cells.

It should be appreciated that the invention is not limited to the particular embodiments described and illustrated herein but includes all modifications and variations falling within the scope of the invention as defined in the appended claims.

What is claimed is:

1. A topical biophotonic material comprising: a cohesive matrix, wherein the cohesive matrix comprises silicone and sodium hyaluronate, and Eosin Y, and wherein the topical biophotonic material is elastic, and substantially translucent.

2. The topical biophotonic material of claim 1, wherein the topical biophotonic material is a peelable film.

3. The topical biophotonic material of claim 1, wherein the tear and/or tensile strength of the topical biophotonic material is greater than an adhesive strength of the topical biophotonic material to a surface to which it is applied.

4. The topical biophotonic material of claim 1, wherein the topical biophotonic material has a pre-formed configuration.

5. The topical biophotonic material of claim 1, wherein the pre-formed configuration has a shape and/or a size corresponding with a shape and/or a size of a body part to which the topical biophotonic material can be applied.

6. The topical biophotonic material of claim 5, wherein the body part is selected from a head, scalp, forehead, nose, cheeks, ears, lip, face, neck, shoulder, arm pit, arm, elbow, hand, finger, abdomen, chest, stomach, back, sacrum, buttocks, genitals, legs, knee, feet, nails, hair, toes, boney prominences, and combinations thereof.

7. The topical biophotonic material of claim 4, wherein the topical biophotonic material is a mask.

8. The topical biophotonic material of claim 7, wherein the mask is a face mask having at least one opening for the eyes, nose or mouth.

9. The topical biophotonic material of claim 4, wherein the pre-formed configuration is a shape and/or a size corresponding with a shape and/or a size of a light source or lamp to which the topical biophotonic material can be attached.

10. The topical biophotonic material of claim 1, wherein the topical biophotonic material can be removed without leaving substantially any residue on a surface to which the topical biophotonic material is applied.

11. The topical biophotonic material of claim 1, wherein the Eosin Y is within the cohesive matrix.

12. The topical biophotonic material of claim 1, wherein the cohesive matrix is in particulate form.

13. The topical biophotonic material of claim 1, wherein the cohesive matrix further comprises at least one additional polymer.

14. The topical biophotonic material of claim 1, wherein the sodium hyaluronate is present in an amount of about 2 wt % to about 8 wt %.

15. The topical biophotonic material of claim 1, further comprising a compound selected from the group consisting of hydrogen peroxide, carbamide peroxide and benzoyl peroxide.

16. A method for biophotonic treatment of a skin disorder comprising:

placing a topical biophotonic material over a target skin tissue, wherein the topical biophotonic material is elastic and comprises Eosin Y and a cohesive matrix, wherein the cohesive matrix comprises silicone and sodium hyaluronate; and illuminating said topical biophotonic material with light having a wavelength that overlaps with an absorption spectrum of Eosin Y;

wherein the topical biophotonic material is substantially translucent and emits fluorescence at a wavelength and intensity that promotes healing of said skin disorder.

17. A method for biophotonic treatment of acne, comprising:

placing a topical biophotonic material over a target skin tissue, wherein the topical biophotonic material is elastic and comprises Eosin Y and a cohesive matrix, wherein the cohesive matrix comprises silicone and sodium hyaluronate; and illuminating said biophotonic material with light having a wavelength that overlaps with an absorption spectrum of Eosin Y;

wherein the topical biophotonic material is substantially translucent and emits fluorescence at a wavelength and intensity that treats the acne.

18. A method for promoting wound healing comprising:

placing a topical biophotonic material over or within a wound, wherein the topical biophotonic material is elastic and comprises Eosin Y and a cohesive matrix, wherein the cohesive matrix comprises silicone and sodium hyaluronate; and illuminating said biophotonic material with light having a wavelength that overlaps with an absorption spectrum of Eosin Y;

wherein the topical biophotonic material is substantially translucent and emits fluorescence at a wavelength and intensity that promotes wound healing.

19. A method for promoting skin rejuvenation comprising:

placing a topical biophotonic material over a target skin tissue, wherein the topical biophotonic material is elastic and comprises Eosin Y and a cohesive matrix, wherein the cohesive matrix comprises silicone and sodium hyaluronate; and illuminating said biophotonic material with light having a wavelength that overlaps with an absorption spectrum of Eosin Y;

wherein the topical biophotonic material is substantially translucent and emits fluorescence at a wavelength and intensity that promotes skin rejuvenation.

20. The method of any one of claim 16, 17, 18 or 19, wherein the biophotonic material is removed after illumination.

21. The method of any one of claim 16, 17, 18 or 19, wherein the biophotonic material is peelable and is peeled off.

* * * * *